(12) United States Patent
Bravo et al.

(10) Patent No.: US 9,549,819 B1
(45) Date of Patent: Jan. 24, 2017

(54) PREFORMED CRANIAL IMPLANT

(71) Applicant: DePuy Synthes Products, Inc., Raynham, MA (US)

(72) Inventors: Joseph Bravo, Little Egg Harbor, NJ (US); Bryan James Griffiths, West Chester, PA (US); Eric B. Reno, West Chester, PA (US); Stanley Kniezewski, West Chester, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 14/746,008

(22) Filed: Jun. 22, 2015

Related U.S. Application Data

(60) Provisional application No. 62/015,816, filed on Jun. 23, 2014.

(51) Int. Cl.
 *A61F 2/28* (2006.01)
 *A61F 2/00* (2006.01)
 *A61B 19/02* (2006.01)

(52) U.S. Cl.
 CPC ........... *A61F 2/2875* (2013.01); *A61B 19/026* (2013.01); *A61F 2/0063* (2013.01)

(58) Field of Classification Search
 CPC .............................. A61F 2/2875; A61F 2/0063
 USPC .............. 606/151, 285, 284; 623/17.19
 See application file for complete search history.

(56) References Cited

U.S. PATENT DOCUMENTS

| | | | |
|---|---|---|---|
| 14,887 A | 5/1856 | Seymour | |
| RE2,793 E | 10/1867 | Patterson | |
| 1,788,382 A | 1/1931 | Cushwa | |
| 3,213,658 A | 10/1965 | Arthur | |
| 3,457,761 A | 7/1969 | Brosseit | |
| 4,413,497 A | 11/1983 | Kubis et al. | |
| 5,468,242 A * | 11/1995 | Reisberg ............ | A61B 17/8085 606/151 |
| 5,743,913 A * | 4/1998 | Wellisz .............. | A61B 17/8061 606/285 |

(Continued)

OTHER PUBLICATIONS

Kramer PhD, et al., Anatomical Background for the Development of Preformed Cranioplasty Implants, Journal of Craniofacial Surgery, vol. 24, No. 1, Jan. 2013, 5 pages.

(Continued)

*Primary Examiner* — Alvin Stewart
(74) *Attorney, Agent, or Firm* — Baker & Hostetler LLP

(57) ABSTRACT

A surgical fixation device is provided, including a preformed cranial mesh configured to generally conform to a predetermined averaged geometry. The cranial mesh includes a preformed flexible mesh body having opposed inner and outer surfaces, and a plurality of apertures that extend through the mesh body from the outer surface to the inner surface, each of the plurality of apertures extending along a respective central axis from the outer surface to the inner surface. The mesh body is configured as-manufactured to contact the predetermined averaged geometry at least at three spaced apart locations, such that 1) no portion of the mesh body crosses the predetermined averaged geometry in a first direction from the outer surface toward the inner surface, and 2) no location on the inner surface of the mesh body is spaced from the predetermined averaged geometry a distance greater than a select distance along the first direction.

30 Claims, 17 Drawing Sheets

(56) References Cited

U.S. PATENT DOCUMENTS

| | | | | |
|---|---|---|---|---|
| 5,752,958 | A * | 5/1998 | Wellisz | A61B 17/8085 606/280 |
| 5,766,176 | A * | 6/1998 | Duncan | A61B 17/8085 606/281 |
| 5,980,540 | A * | 11/1999 | Bruce | A61B 17/8085 606/151 |
| 6,071,291 | A * | 6/2000 | Forst | A61B 17/8085 606/151 |
| 6,093,188 | A * | 7/2000 | Murray | A61B 17/8004 606/282 |
| 7,655,047 | B2 | 2/2010 | Swords | |
| 7,662,155 | B2 * | 2/2010 | Metzger | A61B 17/8085 606/280 |
| 8,246,663 | B2 * | 8/2012 | Lovald | A61B 17/8071 606/280 |
| 8,337,533 | B2 * | 12/2012 | Raines | A61B 17/8057 606/284 |
| 9,220,597 | B2 * | 12/2015 | Engstrand | A61F 2/28 |
| D751,202 | S * | 3/2016 | Gabele | A61F 2/28 D24/155 |
| 2005/0149032 | A1 * | 7/2005 | Vaughen | A61B 17/8085 606/77 |
| 2008/0009872 | A1 | 1/2008 | Vaughen et al. | |
| 2009/0216338 | A1 * | 8/2009 | Gingras | A61F 2/0063 623/23.72 |
| 2014/0316472 | A1 * | 10/2014 | Rise | A61B 17/8085 606/281 |
| 2015/0105806 | A1 * | 4/2015 | Dorafshr | A61F 2/2875 606/151 |

OTHER PUBLICATIONS

OsteoMed, OsteoForm, Formable Craniofacial Mesh, Brochure, accessed at http://www.osteomed.com/Neuro/OsteoFormMesh.htm on Apr. 17, 2014, 2 pages.

* cited by examiner

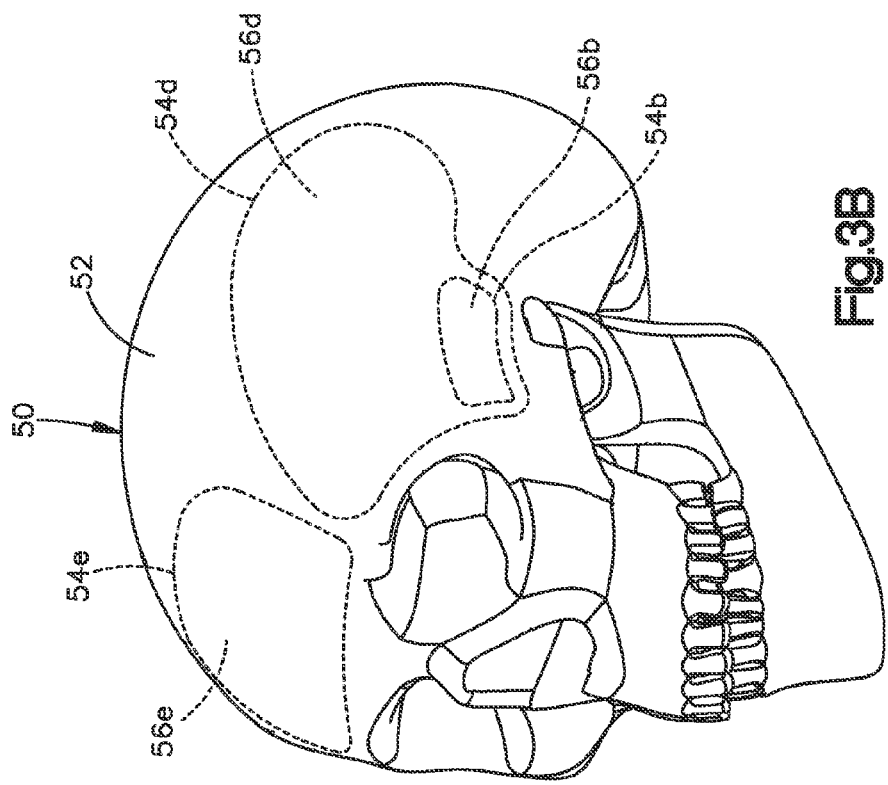
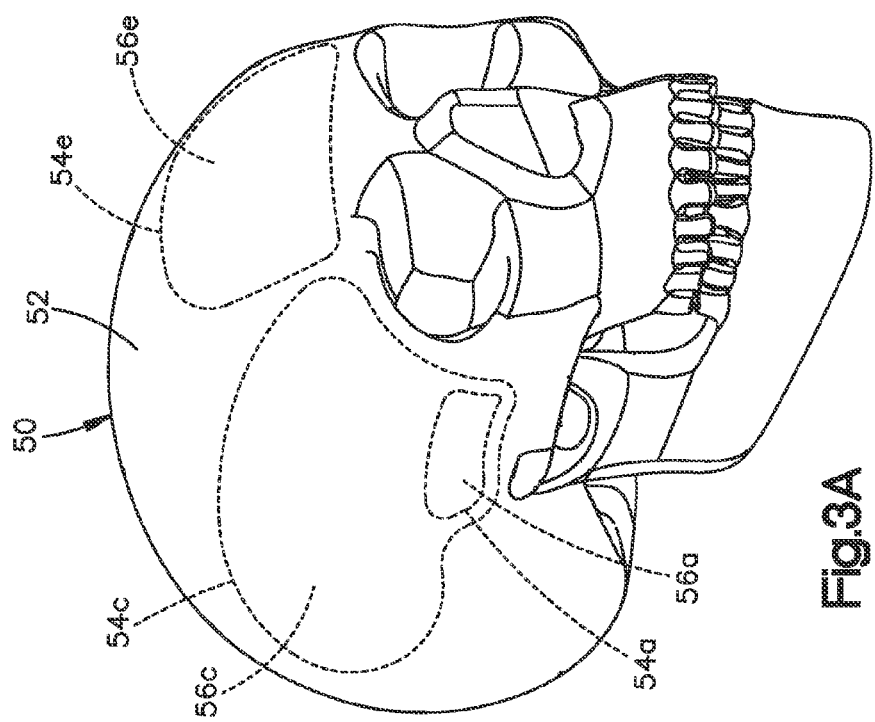

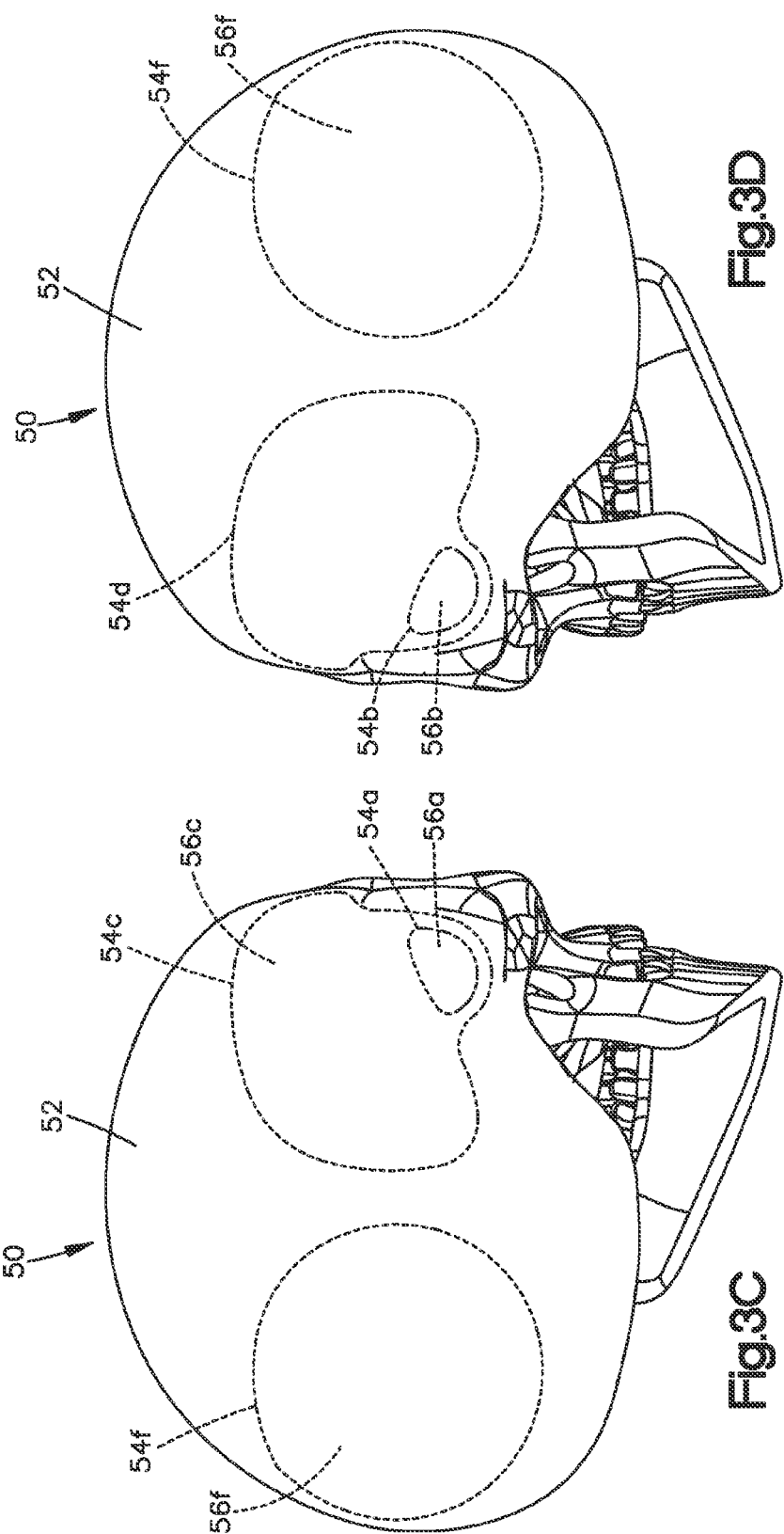

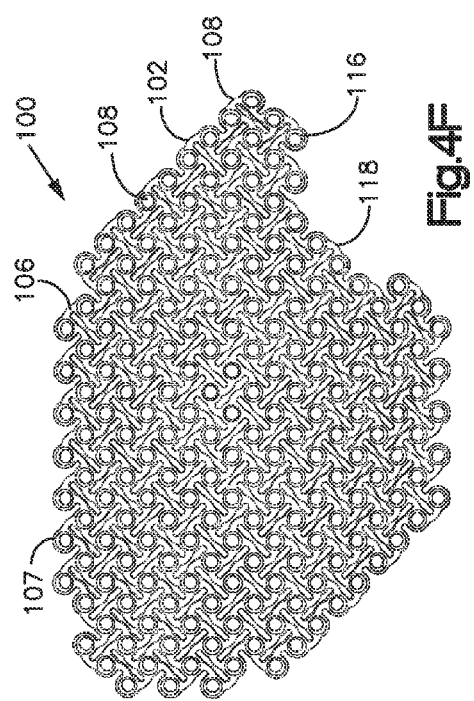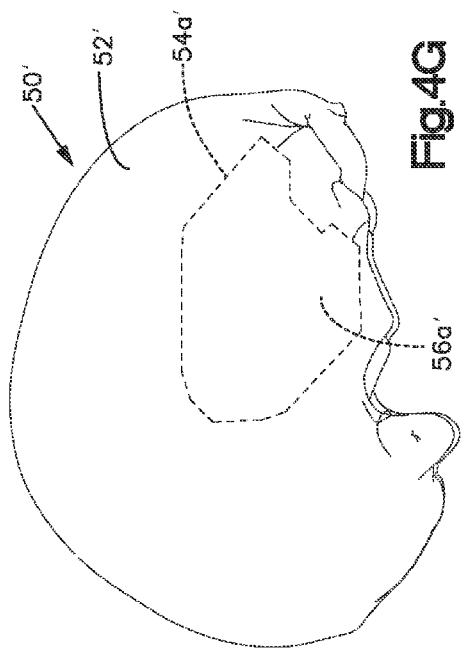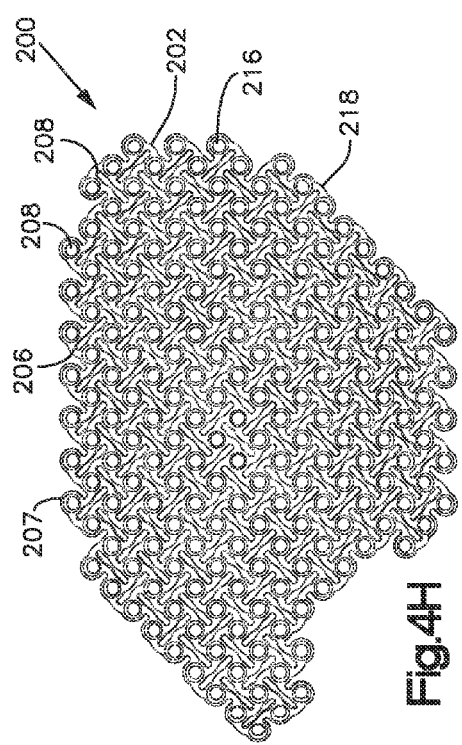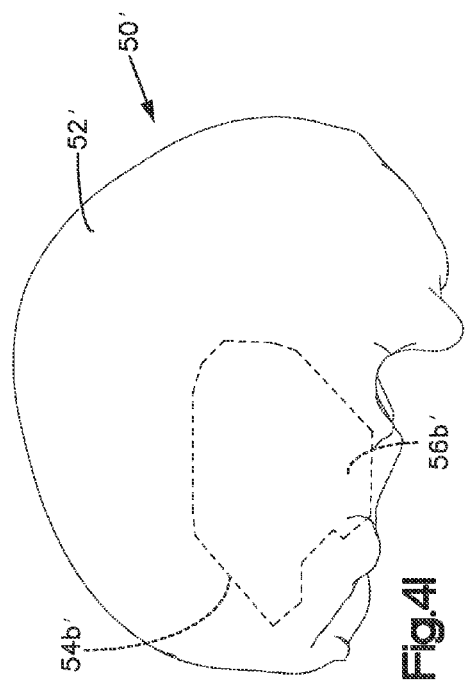

PREFORMED CRANIAL IMPLANT

CROSS REFERENCE TO RELATED APPLICATIONS

This application claims benefit to U.S. Provisional Application No. 62/015,816, filed Jun. 23, 2014, the disclosure of which is hereby incorporated by reference in its entirety.

TECHNICAL FIELD

The present application relates generally to a surgical fixation device for bone reconstruction. More specifically, the present application relates to a contoured fixation device that is contoured in three dimensions to approximate a geometry defined by a region of bone to which the fixation device may be attached.

BACKGROUND

Biologically compatible metallic meshes capable of being formed and contoured to the three-dimensional skeletal anatomy are known for surgical use. These meshes have been employed in osteosynthesis to rejoin and repair bone discontinuities resulting from trauma (i.e., fractures) and/or surgical procedures wherein osteotomies of the bone are necessary to performing the procedure.

Various configurations of contourable fixation devices have been used that are commonly secured to a region of bone with fasteners, for example bone screws. One class of contourable fixation device includes closed, solid construct meshes that are formed by machining, chemically etching, or otherwise creating a plurality of circular fastener openings into a generally square and flat sheet of material. These closed, solid construct meshes have limited flexibility and limited three-dimensional contourability due to their generally solid or closed structures. Accordingly, these closed, solid construct meshes can be difficult to three-dimensionally contour to correspond closely to a geometry that matches a geometry of an irregular or intricate portion of skeletal anatomy while avoiding kinking. Kinking is undesirable because it can cause a non-aesthetic appearance, soft tissue irritation, and other problems.

To attempt to eliminate the kinking problem and improve contourability, surgeons typically find it necessary to cut out multiple and/or extensive portions of the closed, solid construct meshes. FIG. 1 shows an example of a prior art closed, solid construct mesh 20 having triangular relief cuts 22 typically made by surgeons for applying this type of mesh to a frontal region of a skull. One drawback of making such customized relief cutouts is extended surgical time. Another drawback is that the cutouts themselves reduce the strength of the final mesh construct because the narrow section at the center of the mesh along line A-A has decreased flexural rigidity.

Another class of contourable fixation device is characterized by an open-structured, highly contourable mesh for example as disclosed in U.S. Pub. Nos. 2005/0149032 and 2008/0009872, the disclosures of which are hereby incorporated by reference in their entireties. FIG. 2 shows an example of a prior art open-structured, highly contourable mesh 30 in an initial rigid and flat two-dimensional configuration (hereinafter initial flat configuration). As shown in FIG. 2, the open-structured, highly contourable mesh 30 includes a plurality of spaced-apart fastening plates 32 (hereinafter plates), deformable links 34 (hereinafter links) interconnecting the plates 32, and openings 36 interspersed between the plates 32. Additionally, the open-structured, highly contourable mesh 30 can define holes 38 that extend through at least some of the plates 32. The holes 38 are configured to receive a fastener, such as a bone screw or tack, to secure the open-structured, highly contourable mesh 30 to a target region of bone.

The openings 36 may be defined by at least a portion of both the links 34 and the plates 32. The openings 36 provide space within the open-structured, highly contourable mesh 30 to allow the links 34 to be deformed in three dimensions. Accordingly, the open-structured, highly contourable mesh 30 is configured to be three-dimensionally contoured without kinking, more easily than the closed, solid construct mesh 20.

Typically, contourable fixation devices, such as the open-structured highly contourable mesh 30 discussed above, are provided to a surgeon housed in a sterile packaging in the initial flat configuration. Providing the contourable fixation device in the initial flat configuration may require the surgeon to spend time during the surgery contouring the fixation device to correspond to the anatomy of the target region of bone to which the fixation device is to be secured.

The process for a surgeon contouring the fixation device during surgery, to match the anatomy of an individual patient, may require a number of lengthy steps including: determining the implant reception site on the bone and the final three-dimensional shape of fixation device based on the anatomical three-dimensional shape of the target region of bone; heating the fixation device to above its glass transition temperature (by any suitable means such as a hot water or saline bath, hot air gun, bender/cutter iron, etc.) to make the fixation device malleable; placing the fixation device directly on the bone reception site and contouring the fixation device to have a desired three-dimensional shape; and cooling the fixation device by allowing its temperature to fall below the glass transition temperature whereupon the mesh returns to a rigid condition and holds the three-dimensional contoured shape.

Thus, an atomically-shaped fixation device that is available for use by a user, such as a surgeon, prior to surgery, without the need for extensive bending or other modification by the surgeon during surgery, and that conforms to a predetermined averaged geometry of a bone region can result in improved aesthetic results as well as a reduction of time and cost associated with a surgical procedure in which the fixation device is used to rejoin and repair bone discontinuities.

SUMMARY

The present application discloses in accordance with one embodiment, a cranial mesh that is configured to generally conform to a predetermined averaged geometry, the cranial mesh including a preformed flexible mesh body having an inner surface, an outer surface opposite the inner surface, and a plurality of apertures that extend through the mesh body from the outer surface to the inner surface, each of the plurality of apertures extending along a respective central axis from the inner surface to the outer surface. The mesh body is configured as-manufactured to contact the predetermined geometry at least at three spaced apart locations, such that 1) no portion of the mesh body crosses the predetermined averaged geometry in a first direction from the outer surface toward the inner surface, and 2) no location on the inner surface of the mesh body is spaced from the predetermined averaged geometry a distance greater than 20 mm along the first direction.

A cranial mesh is also provided that is configured to generally conform to a predetermined averaged geometry, the cranial mesh including a preformed flexible mesh body having an inner surface, an outer surface opposite the inner surface, and a plurality of apertures that extend through the mesh body from the outer surface to the inner surface, each of the plurality of apertures extending along a respective central axis from the inner surface to the outer surface, the preformed mesh including a sidewall that extends between the inner surface and the outer surface, the sidewall defining an outer perimeter of the mesh body, the outer perimeter having a maximum outer dimension measured along a straight line from a first point on the outer perimeter to a second point on the outer perimeter, such that the mesh body does not define an outer dimension measured along a straight line that extends between and terminates at any pair of points on the outer perimeter that is greater than the maximum outer dimension. The preformed mesh body is configured as-manufactured such that when the inner surface contacts the predetermined averaged geometry at least at three spaced apart locations, 1) no portion of the mesh body crosses the predetermined averaged geometry in a direction from the outer surface toward the inner surface, and 2) no location on the inner surface is spaced from the predetermined averaged geometry a distance greater than 10 percent of the maximum outer dimension as measured along a straight line that defines a shortest distance to the predetermined averaged geometry.

A kit of preformed cranial meshes is also provided, each of the preformed cranial meshes configured to generally conform to different regions of a predetermined averaged geometry, the kit including a first preformed flexible cranial mesh having a first inner surface, a first outer surface that is opposite the first inner surface, and a first plurality of apertures that extend from the first outer surface to the first inner surface, the first preformed flexible cranial mesh configured as-manufactured such that when the first inner surface contacts a first region of the predetermined averaged geometry, no location on the first inner surface is spaced from the predetermined averaged geometry by more than 20 mm. The kit further including a second preformed flexible cranial mesh having a second inner surface, a second outer surface that is opposite the second inner surface, and a second plurality of apertures that extend from the second outer surface to the second inner surface, the second preformed cranial mesh configured as-manufactured such that when the second inner surface contacts a second region of the predetermined averaged geometry that is spaced from the first region, no location on the second inner surface is spaced from the predetermined averaged geometry by more than 20 mm.

BRIEF DESCRIPTION OF THE DRAWINGS

The foregoing summary, as well as the following detailed description of illustrative embodiments of the fixation device of the present application, will be better understood when read in conjunction with the appended drawings. For the purposes of illustrating the fixation device of the present application, there is shown in the drawings illustrative embodiments. It should be understood, however, that the application is not limited to the precise arrangements and instrumentalities shown. In the drawings:

FIG. 3A is a perspective view of a skull;

FIG. 3B is another perspective view of the skull illustrated in FIG. 3A;

FIG. 3C is another perspective view of the skull illustrated in FIG. 3A;

FIG. 3D is another perspective view of the skull illustrated in FIG. 3A;

FIG. 4F is a top plan view of the fixation device illustrated in FIG. 4C, the fixation device shown in the second contoured configuration;

FIG. 4G is a first side elevation view of a portion of a population averaged skull;

FIG. 4H is top plan view of a fixation device according to another embodiment, the fixation device shown in the second contoured configuration;

FIG. 4I is a second side elevation view of the portion of the population averaged skull illustrated in FIG. 4G;

DETAILED DESCRIPTION OF ILLUSTRATIVE EMBODIMENTS

Figure 1:
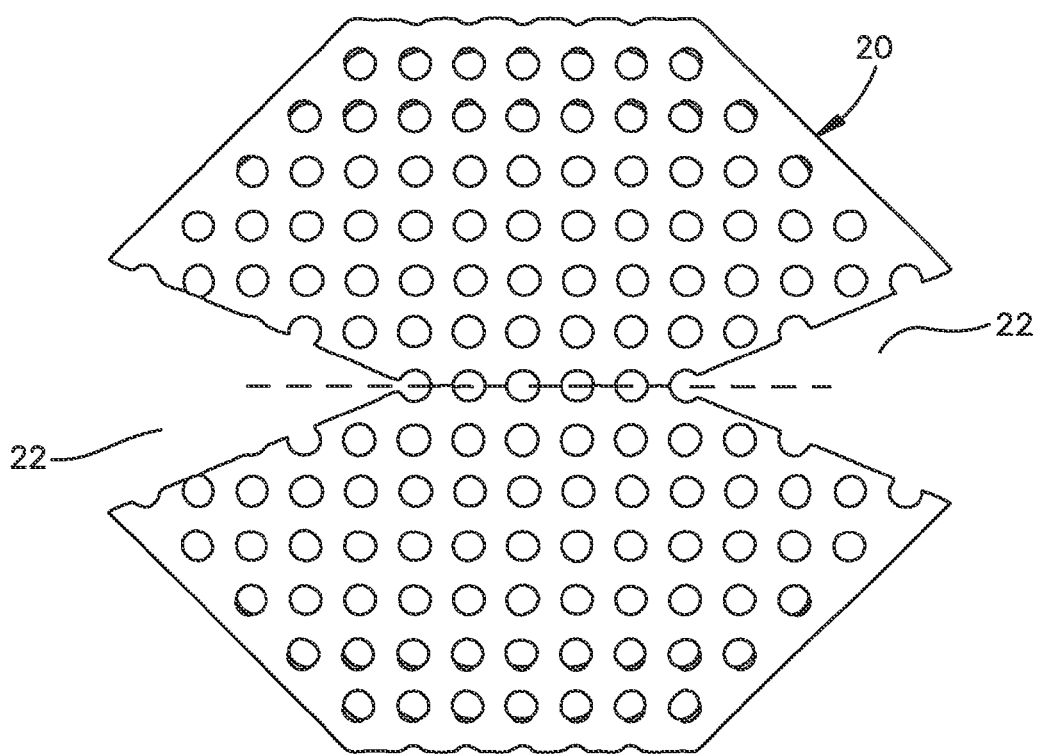
FIG. 1 is a top plan view of a closed, solid construct mesh of the prior art showing typical relief cutouts made by surgeons to three-dimensionally shape the mesh to the anatomical shape of a target bone.
Figure 2:
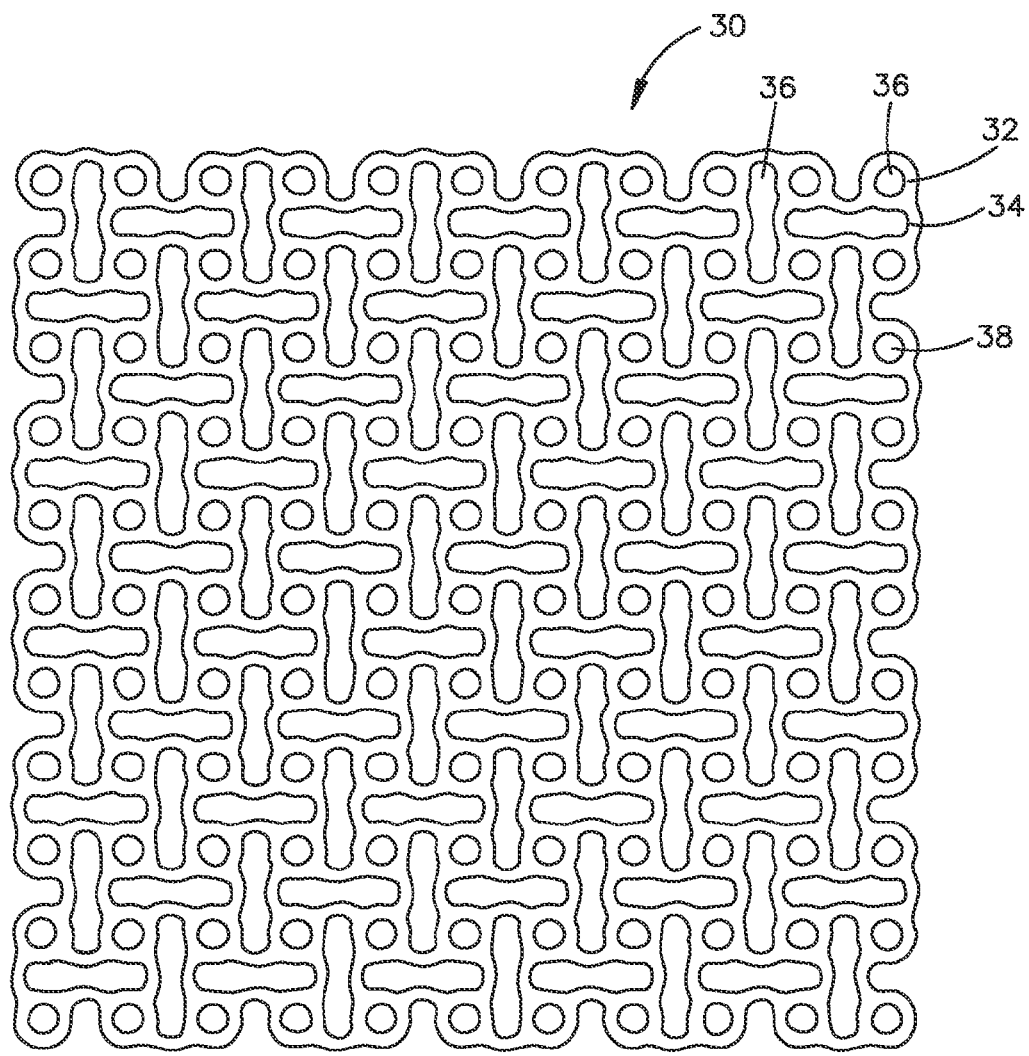
FIG. 2 is a top plan view of an open-structured, highly contourable mesh of the prior art in an initial rigid and flat two-dimensional configuration.

Certain terminology is used in the following description for convenience only and is not limiting. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. Further, reference to values stated in ranges includes each and every value within that range. All ranges are inclusive and combinable. Certain features of the invention which are described herein in the context of separate embodiments may also be provided in combination in a single embodiment. Conversely, various features of the invention that are described in the context of a single embodiment may also be provided separately or in any subcombination.

A radial or polar coordinate system is provided and described herein. The polar coordinate system includes a two dimensional radial plane that is centered on and normal to a reference axis, for instance a central axis of an aperture. The polar coordinate system defines a radial component that is measured as the distance from the reference axis along the plane. The words "proximate" and "distal" designate locations closer to and farther away from the reference axis respectively. The polar coordinate system further defines an angular component that is measured as the angular position about the reference axis.

Referring to FIGS. 3A-3D, solid objects have an outer surface that is a continuous boundary which divides a three-dimensional space into two regions, a first region inside the solid object and a second region outside the solid object. The shape of the outer surface defines a geometry, which is a two dimensional area. The geometry of an outer surface of a solid object can be simple, for example the geometry of a single surface of a cube is a flat square. The geometry of an outer surface of a solid object can also be complex, for example a human skull 50, can include an outer surface 52 that is contoured in three dimensions with one or more concavities and one or more convexities.

As shown in FIGS. 3A-3D, the outer surface 52 of the skull 50 can define a plurality of regions 54. In one embodiment, the plurality of regions 54 can include a first region 54a that is defined by at least a portion of a temporal bone on one side (for example the right side) of the skull 50, a second region 54b that is defined by at least a portion of a temporal bone on the other side (for example the left side) of the skull 50, a third region 54c that is defined by at least a portion of the frontal, temporal, and parietal bones on the one side of the skull 50, a fourth region 54d that is defined by at least a portion of the frontal, temporal, and parietal bones on the other side of the skull 50, a fifth region 54e that is defined by at least a portion of the frontal bone of the skull 50, and a sixth region 54f that is defined by at least a portion of the parietal bone of the skull 50. Some of the plurality of regions 54, for example the first region 54a and the third region 54c can overlap. It will be understood that various other regions of the skull 50 defined by one or more of the bones of the skull 50 could also be defined.

The outer surface 52 of the skull 50 in each of the plurality of regions 54 defines a respective geometry 56. For example the outer surface 52 within the first region 54a defines a first geometry 56a, the outer surface 52 within the second region 54b defines a second geometry 56b, and so on through each of the plurality of regions 54. Each of the respective geometries 56 is a two-dimensional shape, for example a plane having a length and a width but no depth, the plane being contoured in three dimensions.

In one embodiment, the geometry of similar regions across multiple solid objects can be averaged to arrive at a predetermined averaged geometry as described, for example, in the article "Anatomical Background for the Development of Preformed Cranioplasty Implants" by Drs. Kamer, Noser, and Hammer, Journal of Craniofacial Surgery, Volume 24, Number 1, Jan. 2013," the disclosure of which is hereby incorporated by reference in its entirety. For example, one or more of the first geometry 56a of the first region 54a, the second geometry 56b of the second region 54b, of the third geometry 56c of the third region 54c, the fourth geometry 56d of the fourth region 54d, the fifth geometry 56e of the fifth region 56e, and the sixth geometry 56f of the sixth region 54f of a plurality of human skulls 50 can be averaged to arrive at a population averaged geometry. According to one embodiment, a portion up to an entirety of a population of skulls 50 can be averaged, the portion up to an entirety including one or more of the first region 54a, the second region 54b, the third region 54c, the fourth region 54d, the fifth region 54e, and the sixth region 54f.

Referring to FIGS. 4A-4E, a cranial implant, for example a cranial mesh 100, can include a flexible mesh body 102 (hereinafter mesh body), the mesh body 102 having an inner surface 104, an outer surface 106 that is opposite the inner surface 104, a sidewall 107 that extends between the inner surface 104 and the outer surface 106. As shown in the illustrated embodiment, the inner surface 104 is the mirror image of the outer surface 106, and vice versa. In another embodiment the inner surface 104 is not the mirror image of the outer surface 106. The cranial mesh 100 can further include a plurality of apertures 108 that each defines a respective central axis 110. Each of the plurality of apertures 108 extends along the respective central axis 110 from the inner surface 104 to the outer surface 106.

Figure 4A:
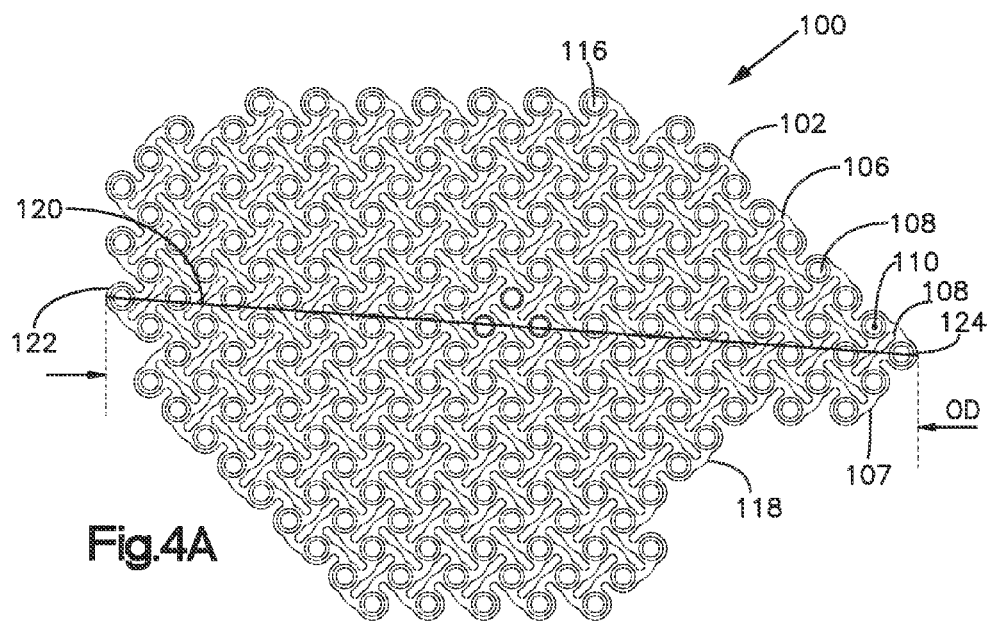
FIG. 4A is a top plan view of a fixation device according to one embodiment, the fixation device shown in a first flat configuration.
Figure 4B:
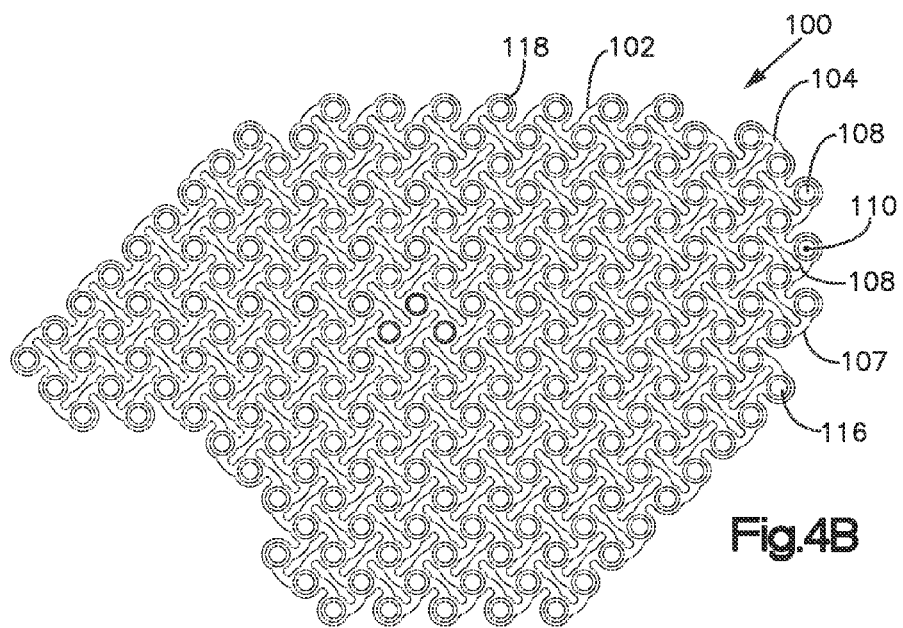
FIG. 4B is a bottom plan view of the fixation device illustrated in FIG. 4A, the fixation device shown in the first flat configuration.
Figure 4C:
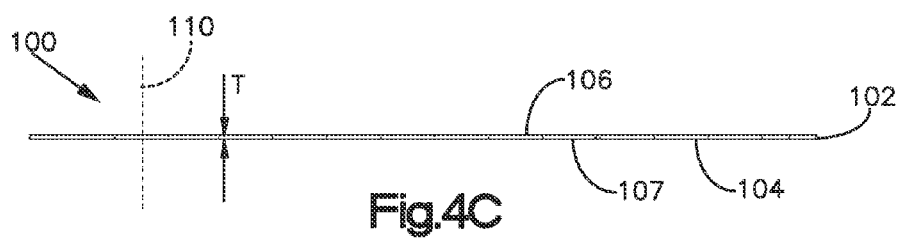
FIG. 4C is a side elevation view of the fixation device illustrated in FIG. 4A, the fixation device shown in the first flat configuration.
Figure 4D:
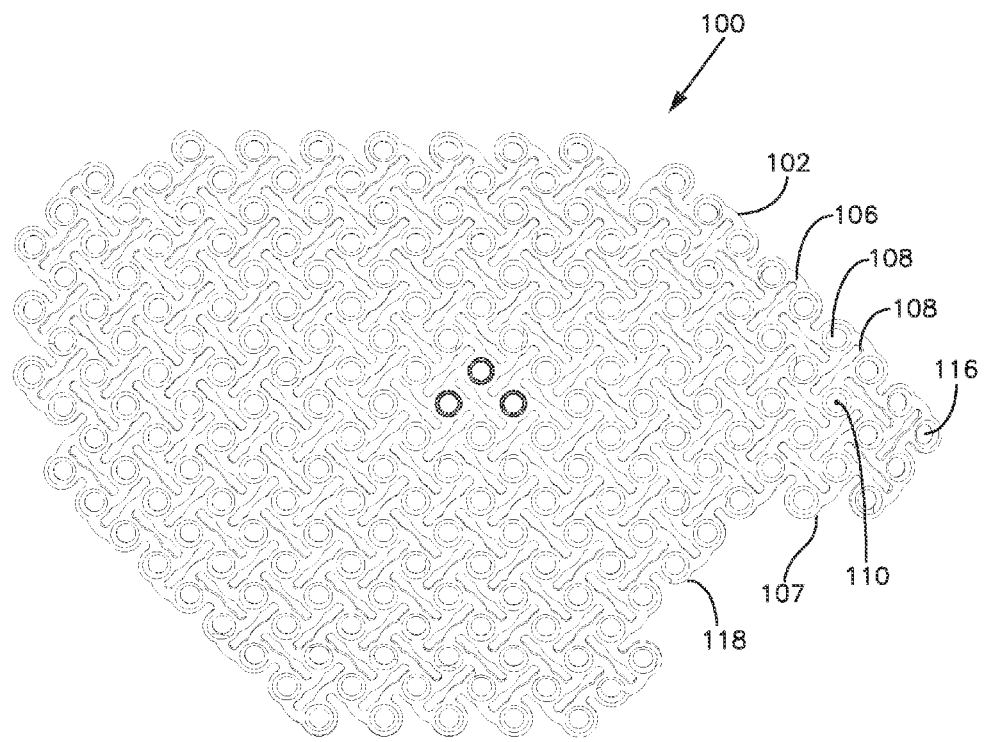
FIG. 4D is a top plan view of the fixation device illustrated in FIG. 4A, the fixation device shown in a second contoured configuration.
Figure 4E:
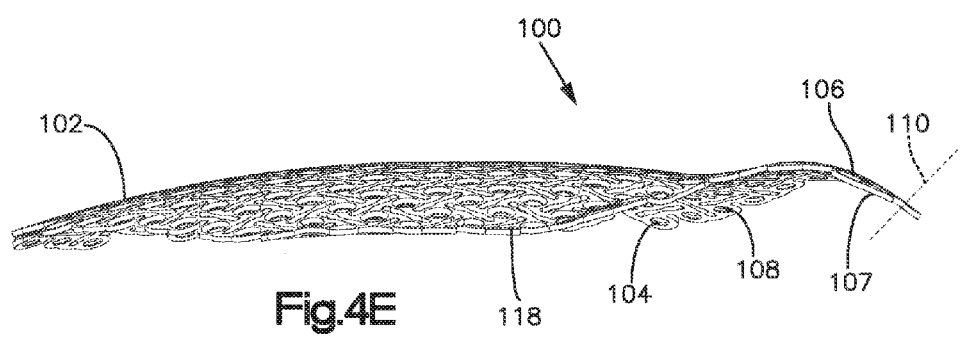
FIG. 4E is a side elevation view of the fixation device illustrated in FIG. 4D, the fixation device shown in the second contoured configuration.

Referring to FIGS. 4A to 4C, the cranial mesh 100 has a first, flat configuration in which the inner surface 104 and the outer surface 106 are each substantially flat. Referring to FIGS. 4D to 4E, the cranial mesh 100 has a second, contoured configuration in which the inner surface 104 is contoured in three dimensions such that the cranial mesh 100 generally conforms to a geometry. Referring to FIGS. 3A-3D and 4D to 4E, in accordance with one embodiment when the cranial mesh 100 is in the second, contoured configuration, the inner surface 104 generally conforms to the first geometry 56a of the first region 54a of the skull 50. In accordance with another embodiment, the first geometry 56a is an averaged first geometry 56a of a plurality of first regions 54a of a plurality of skulls 50.

Referring to FIGS. 4F to 4G, when the cranial mesh 100 is in the second, contoured configuration the cranial mesh 100 can be aligned with a geometry, for example a predetermined averaged geometry to check that the cranial mesh 100 as-manufactured contacts the predetermined averaged geometry at least at one location, for example three spaced apart locations, such that 1) no portion of the mesh body 102 crosses the predetermined averaged geometry in a first direction from the outer surface 106 toward the inner surface 104, and 2) no location on the inner surface 104 of the mesh body 102 is spaced from the predetermined averaged geometry a distance greater than 20 mm along the first direction.

According to one embodiment, the predetermined averaged geometry is defined by a portion up to an entirety of a population averaged skull 50'. The population averaged skull 50' includes an outer surface 52' and a first region 54a'. The outer surface 52' in the first region 54a' can define a first population averaged geometry 56a'.

Once the cranial mesh 100 is in the second, contoured configuration the cranial mesh 100 can be positioned adjacent the predetermined averaged geometry, for example the first population averaged geometry 56a' of the population averaged skull 50', such that the cranial mesh 100 contacts the outer surface 52' of the skull 50' at least at one location, for example at three spaced apart locations about an outer perimeter 118 of the cranial mesh 100. Once the cranial mesh 100 and the skull 50' are aligned and secured against relative movement with respect to one another, a depth gage can be inserted along the central axis 110 of one or more of the apertures 108 to check the distance between the outer surface 52' of the skull 50' and the cranial mesh 100.

Referring to FIGS. 4A to 4G, according to one embodiment, the cranial mesh 100 can be configured to generally conform to a first geometry 56a, for example the first population averaged geometry 56a'. The cranial mesh 100 includes a preformed flexible mesh body 102 having an inner surface 104, an outer surface 106 opposite the inner surface 104, and a plurality of apertures 108 that extend through the mesh body 102 from the outer surface 106 to the inner surface 104, each of the plurality of apertures 108 extending along a respective central axis 110 from the outer surface 106 to the inner surface 104. The mesh body 102 can further be configured as-manufactured to contact the predetermined averaged geometry at a number of spaced apart locations, for example at least three location spaced about the outer perimeter 118, such that 1) no portion of the mesh body 102 crosses the predetermined averaged geometry in a first direction from the outer surface 106 toward the inner surface 104, and 2) no location on the inner surface 104 of the mesh body is spaced from the predetermined averaged geometry a distance greater than 20 mm along the first direction.

According to another embodiment, the mesh body 102 can be configured as-manufactured to contact the predetermined averaged geometry at a number of spaced apart locations, for example at least three locations, such that 1) no portion of the mesh body 102 crosses the predetermined averaged geometry in a first direction from the outer surface 106 toward the inner surface 104, and 2) no location on the inner surface 104 of the mesh body 102 is spaced from the predetermined averaged geometry a distance greater than 10 mm along the first direction. According to another embodiment, the mesh body 102 can be configured as-manufactured to contact the predetermined averaged geometry at a number of spaced apart locations, for example at least three locations, such that 1) no portion of the mesh body 102 crosses the predetermined averaged geometry in a first direction from the outer surface 106 toward the inner surface 104, and 2) no location on the inner surface 104 of the mesh body 102 is spaced from the predetermined averaged geometry a distance greater than 3 mm along the first direction.

The term "as-manufactured" used herein refers to the state of the cranial mesh 100 as it leaves the manufacturer, as opposed to when the cranial mesh 100 is actually in use, for example being implanted by a surgeon. The term "as-manufactured" additionally refers to the cranial mesh 100 in a condition that is devoid of any external force applied by a user, for example a surgeon, nurse, etc., over a portion up to an entirety of the cranial mesh 100 to manipulate the cranial mesh 100 so as to change the shape of the cranial mesh 100, for example to correspond to the anatomy of a specific patient and achieve a close match between the inner surface 104 of the cranial mesh 100 and the predetermined averaged geometry of the patient.

Figure 9:
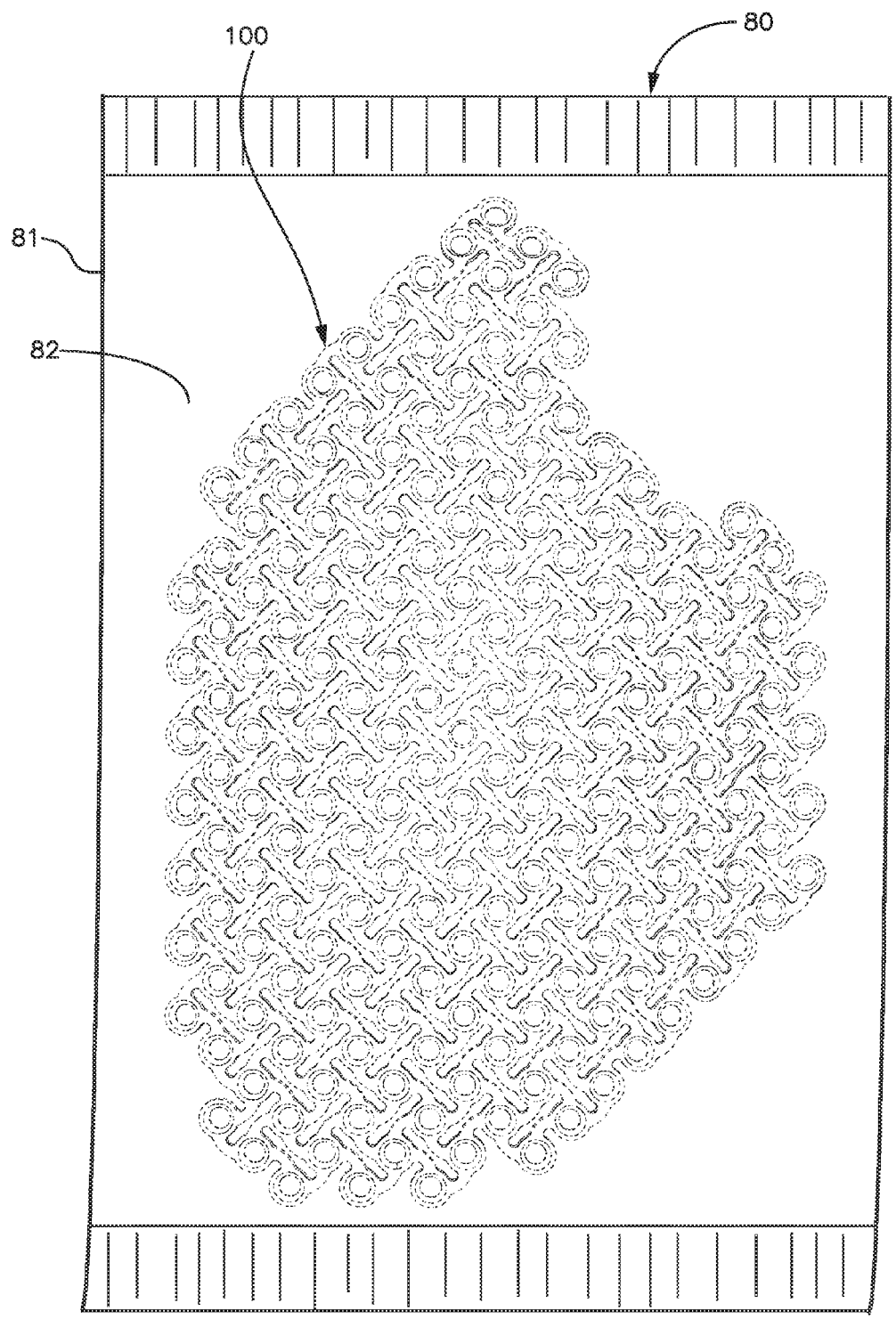
FIG. 9 is a top plan view of a package including a package body defining a sterile enclosed interior, and the fixation device illustrated in FIG. 4D disposed in the sterile enclosed interior, the fixation device in the second, contoured configuration.

Referring to FIG. 9, in one embodiment, the term "as-manufactured" refers to the cranial mesh 100 disposed within a sterile enclosed interior 82 of a package body 81. Accordingly a package 80 is provided, the package 80 comprising a package body 81 defining a sterile enclosed interior 82, and the cranial mesh 100, or any other embodiment of cranial mesh disclosed herein, positioned in the sterile enclosed interior 82, the cranial mesh 100 in the second contoured configuration when it is positioned in the sterile enclosed interior 82. In another embodiment the package 80 comprises a package body 81 defining a box with an interior, a first sterile enclosed interior positioned within the box, a second enclosed sterile interior positioned inside the first enclosed sterile interior, and the cranial mesh 100 in the second contoured configuration positioned in the second enclosed sterile interior. The package 80 can be shipped from the manufacturer to an operating room either directly or through an intermediary such as a distributor.

Referring again to FIGS. 4F to 4G, according to one embodiment, a distance the inner surface 104 is spaced from the first geometry 56a is measured from a given location on the inner surface 104 to the first geometry 56a along a direction parallel to the respective central axis 110 of a respective one of the plurality of apertures 108 closest to the given location.

Referring to FIG. 4C, the mesh body 102 has a thickness T measured from a first location 114 on the inner surface 104 to the outer surface 106 along a direction parallel to the respective central axis 110 of a respective one of the plurality of apertures 108 closest to the first location of the inner surface 104. According to one embodiment the thickness T is within the range of about 0.8 mm to about 0.4 mm, for example about 0.6 mm. The cranial mesh 100 can be formed from any biocompatible material. According to one embodiment, the cranial mesh 100 comprises titanium.

Referring again to FIGS. 4A to 4G, in one embodiment the plurality of apertures 108 includes a plurality of holes 116 that are each configured to receive a fastener that secures the cranial mesh 100 relative to the predetermined averaged geometry. The mesh body 102 can further define an outer perimeter 118 that is defined by the sidewall 107. When the cranial mesh 100 is in the first, flat configuration the outer perimeter 118 has a maximum outer dimension OD measured along a straight line from a first point 122 on the outer perimeter 118 to a second point 124 on the outer perimeter 118, such that the mesh body 102 does not define an outer dimension measured along a straight line that extends between and terminates at any pair of points on the outer perimeter 118 that is greater than the maximum outer dimension OD.

Accordingly, in one embodiment, the cranial mesh 100 is configured to generally conform to a predetermined averaged geometry, the cranial mesh 100 including a preformed flexible mesh body 102 having an inner surface 104, an outer surface 106 opposite the inner surface 104, and a plurality of apertures 108 that extend through the mesh body 102 from the outer surface 106 to the inner surface 104, each of the plurality of apertures 108 extending along a respective central axis 110 from the outer surface 106 to the inner surface 104. The cranial mesh 100 includes a sidewall 107 that extends between the inner surface 104 and the outer surface 106, the sidewall 107 defining an outer perimeter 118 of the mesh body 102, the outer perimeter 118 having a maximum outer dimension OD measured along a straight line 120 from a first point 122 on the outer perimeter 118 to a second point 124 on the outer perimeter 118, such that the mesh body 102 does not define an outer dimension measured along a straight line that extends between and terminates at any pair of points on the outer perimeter 118 that is greater than the maximum outer dimension OD. And, the mesh body 102 is configured as-manufactured such that when the inner surface 104 contacts the predetermined averaged geometry, for example at least at three spaced apart locations, 1) no portion of the mesh body 102 crosses the predetermined averaged geometry in a direction from the outer surface 106 toward the inner surface 104, and 2) no location on the inner surface 104 is spaced from the predetermined averaged geometry a distance greater than 10 percent of the maximum outer dimension OD as measured along a straight line that defines a shortest distance to the predetermined averaged geometry.

According to another embodiment, the mesh body 102 is configured as-manufactured such that when the inner surface 104 contacts the first geometry 56a, for example a predetermined averaged geometry, at least at three spaced apart locations, 1) no portion of the mesh body 102 crosses the predetermined averaged geometry in a direction from the outer surface 106 toward the inner surface 104, and 2) no location on the inner surface 104 is spaced from the predetermined averaged geometry a distance greater than 5 percent of the maximum outer dimension OD as measured along a straight line that defines a shortest distance to the predetermined averaged geometry. According to another embodiment, the mesh body 102 is configured as-manufactured such that when the inner surface 104 contacts the predetermined averaged geometry, for example at least at three spaced apart locations, 1) no portion of the mesh body 102 crosses the predetermined averaged geometry in a direction from the outer surface 106 toward the inner surface 104, and 2) no location on the inner surface 104 is spaced from the predetermined averaged geometry a distance greater than 3 percent of the maximum outer dimension OD as measured along a straight line that defines a shortest distance to the predetermined averaged geometry.

Referring to FIGS. 4H to 4I, a second cranial mesh 200 is provided. The second cranial mesh 200 is similar to the cranial mesh 100 such that the entirety of the description of the cranial mesh 100 above, either in whole or any portion thereof, applies to the second cranial mesh 200. The reference numbers for structural elements in the second cranial mesh 200 that correspond to structural elements in the cranial mesh 100 are increased by one hundred, for example the second cranial mesh 200 can include a flexible mesh body 202, the flexible mesh body 202 having an inner surface 204, an outer surface 206 that is opposite the inner surface 202, a sidewall 207 that extends between the inner surface 204 and the outer surface 206. The second cranial mesh 200 can further include a plurality of apertures 208 that each defines a respective central axis 210. Each of the plurality of apertures 208 extends along the respective central axis 210 from the inner surface 204 to the outer surface 206.

According to one embodiment, the second cranial mesh 200 is the mirror image of the cranial mesh 100. Thus, when the second cranial mesh 200 is in the second, contoured configuration, the inner surface 204 generally conforms to a geometry, for example a second geometry 56b of the second region 54b of the skull 50, which as shown in FIGS. 3A-3D can be on the opposite side of the skull 50 from the first region 54a. As shown in the illustrated embodiment of FIGS. 4H to 4I, when the second cranial mesh 200 is in the second, contoured configuration, the inner surface 204 can generally conform to an averaged second geometry 56b' defined by the second region 54b' of the population averaged skull 50'.

Referring to FIGS. 5A to 5F, a third cranial mesh 300 is provided. The third cranial mesh 300 is similar to the cranial mesh 100 such that the entirety of the description of the cranial mesh 100 above, either in whole or any portion thereof, applies to the third cranial mesh 300. Reference numbers for the structural elements in the third cranial mesh 300 that correspond to structural elements in the cranial mesh 100 have been labeled with reference numbers increased by two hundred. For example the third cranial mesh 300 can include a flexible mesh body 302, the flexible mesh body 302 having an inner surface 304, an outer surface 306 that is opposite the inner surface 302, a sidewall 307 that extends between the inner surface 304 and the outer surface 306. The third cranial mesh 300 can further include a plurality of apertures 308 that each defines a respective central axis 310. Each of the plurality of apertures 308 extends along the respective central axis 310 from the inner surface 304 to the outer surface 306.

According to one embodiment, the third cranial mesh 300 has a different size and shape compared to the cranial mesh 100. Such that when the third cranial mesh 300 is in the second, contoured configuration, the inner surface 304 generally conforms to a third geometry 56c of the third region 54c of the skull 50. The third geometry 56c being different than both the first geometry 56a, the second geometry 56b, and the third geometry 56c. As shown in FIGS. 3A to 3D, the first region 54a and the third region 54c can at least partially overlap. As shown in the illustrated embodiment of FIGS. 5E to 5F, when the third cranial mesh 300 is in the second, contoured configuration, the inner surface 304 can generally conform to an averaged third geometry 56c' defined by the third region 54c' of the population averaged skull 50'.

Figure 5A:
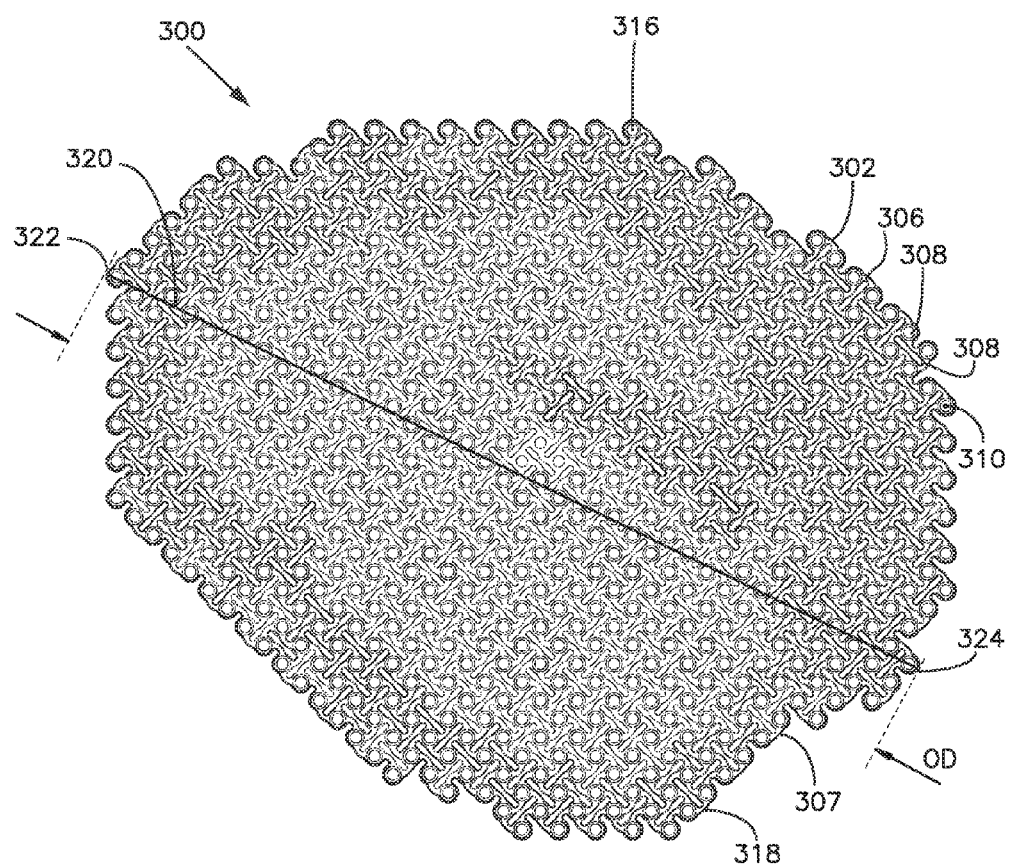
FIG. 5A is a top plan view of a fixation device according to another embodiment, the fixation device shown in the first flat configuration.
Figure 5B:
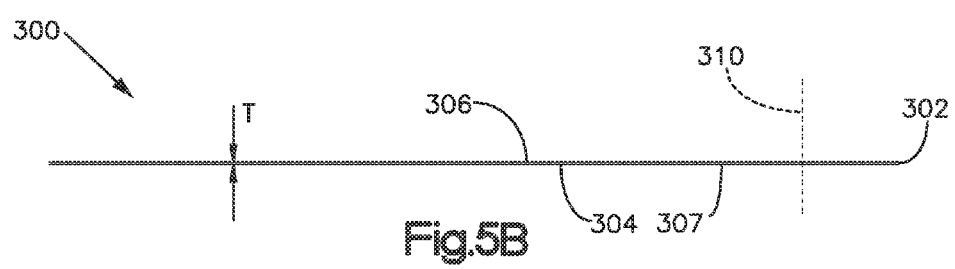
FIG. 5B is a side elevation view of the fixation device illustrated in FIG. 5A, the fixation device shown in the first flat configuration.
Figure 5C:
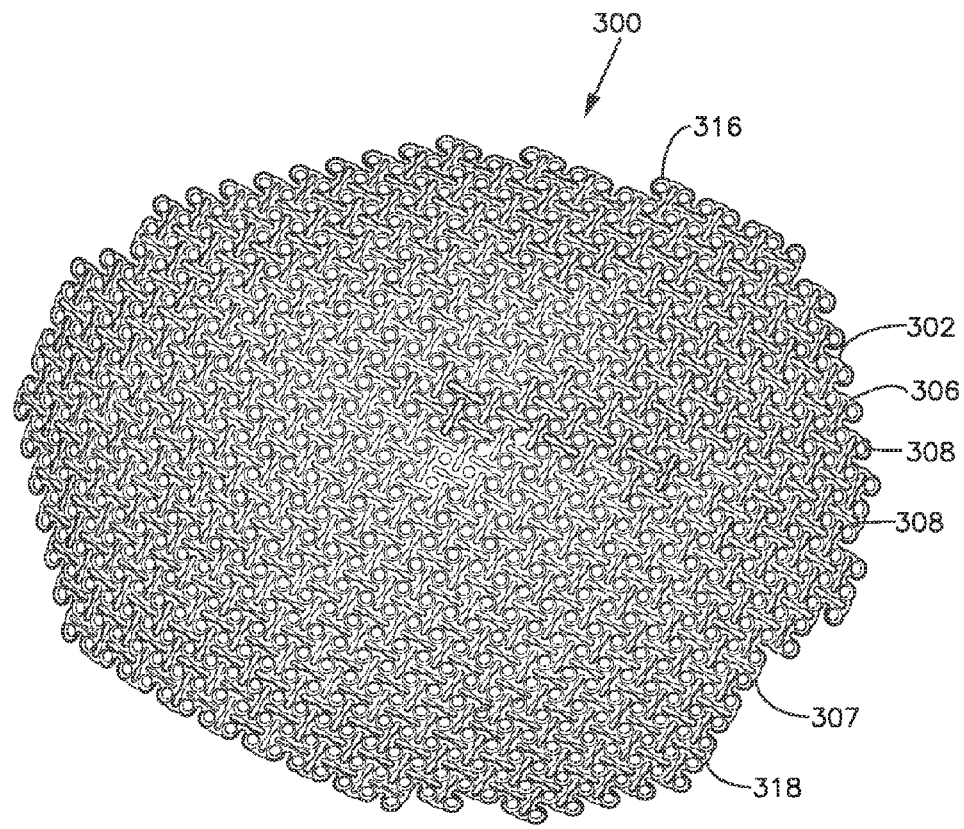
FIG. 5C is a top plan view of the fixation device illustrated in FIG. 4A, the fixation device shown in the second contoured configuration.
Figure 5D:
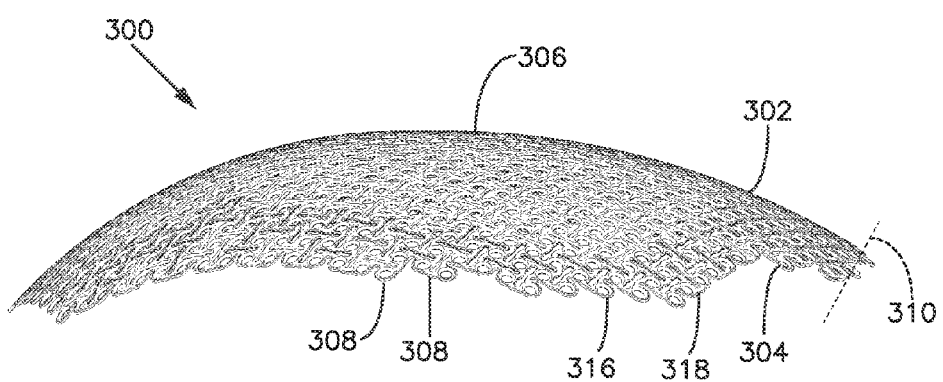
FIG. 5D is a side elevation view of the fixation device illustrated in FIG. 5C, the fixation device shown in the second contoured configuration.
Figure 5E:
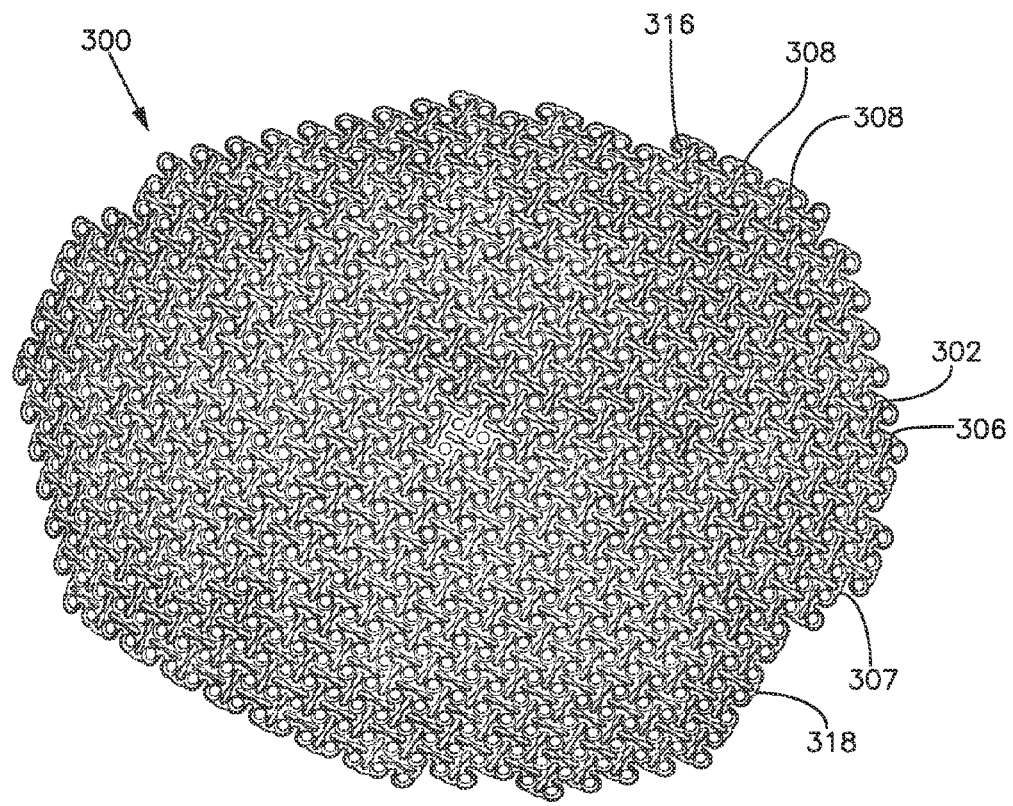
FIG. 5E is a top plan view of the fixation device illustrated in FIG. 5C, the fixation device shown in the second contoured configuration.
Figure 5F:
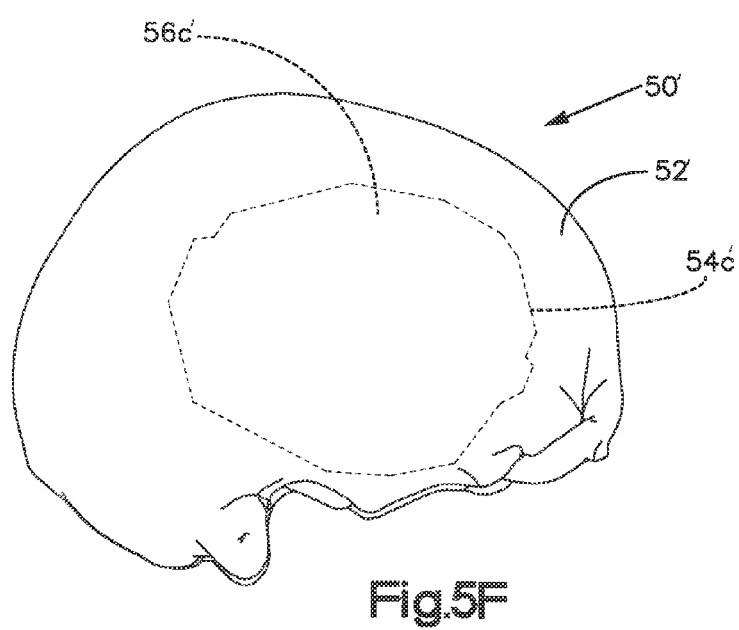
FIG. 5F is a first side elevation view of the portion of the population averaged skull illustrated in FIG. 4G.
Figure 5G:
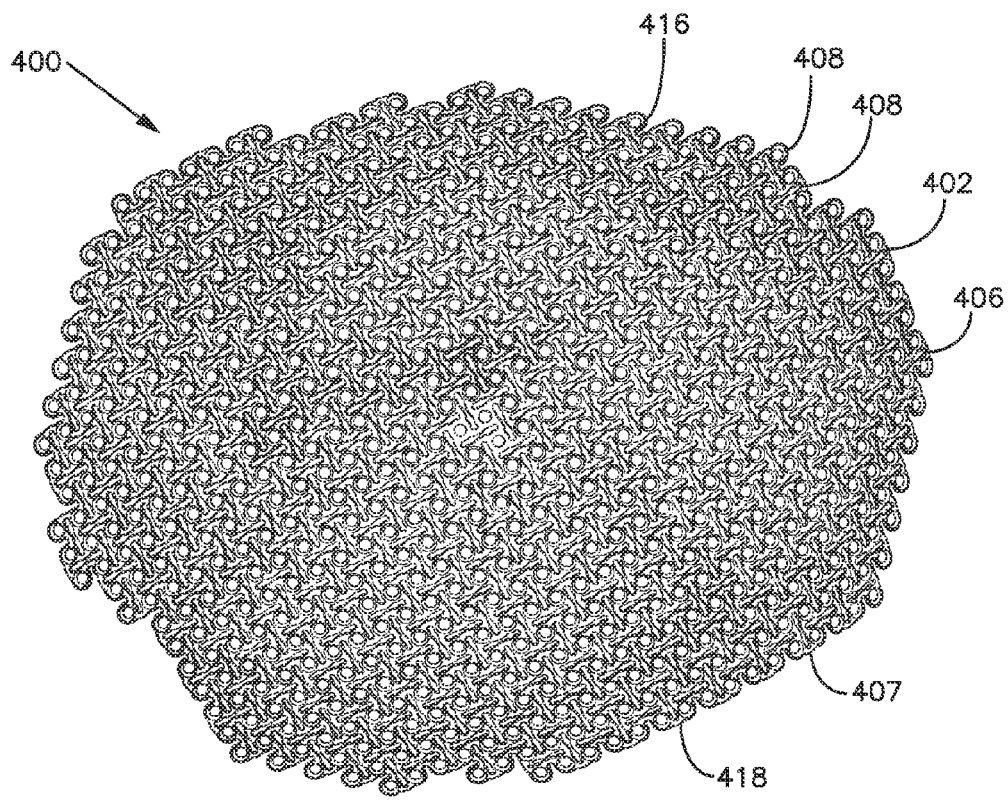
FIG. 5G is top plan view of a fixation device according to another embodiment, the fixation device shown in the second contoured configuration.
Figure 5H:
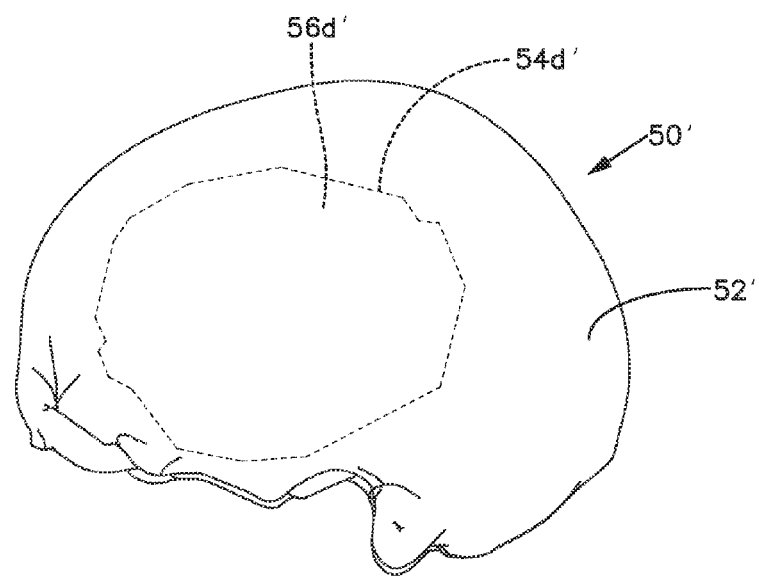
FIG. 5H is a second side elevation view of the portion of the population averaged skull illustrated in FIG. 4G.
Figure 6A:
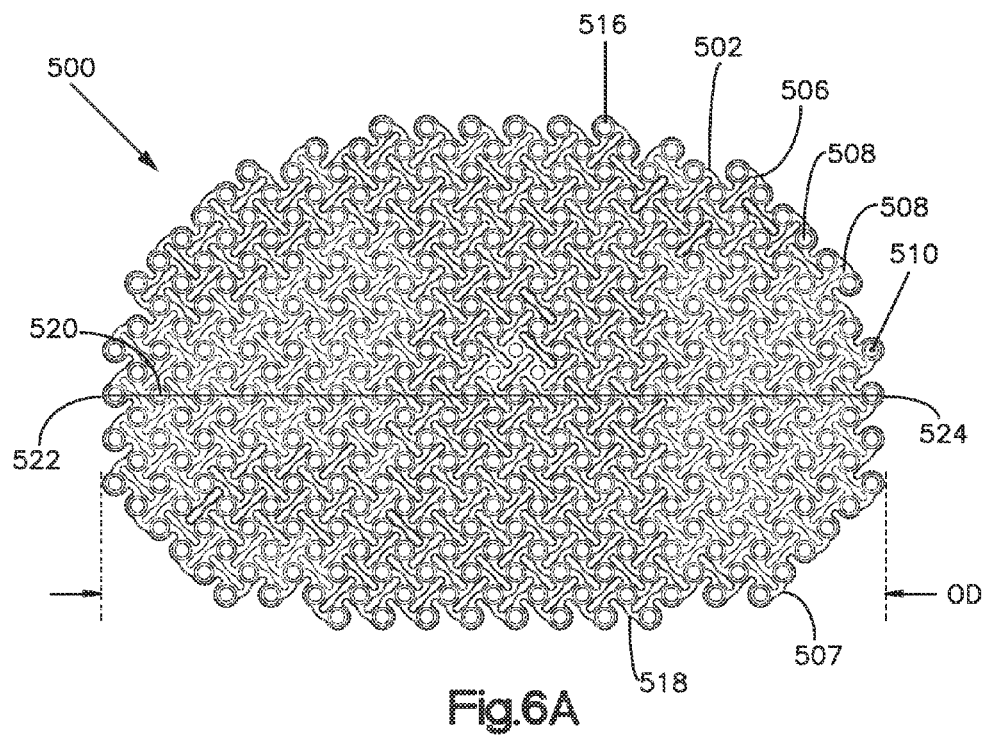
FIG. 6A is a top plan view of a fixation device according to another embodiment, the fixation device shown in the first flat configuration.
Figure 6B:
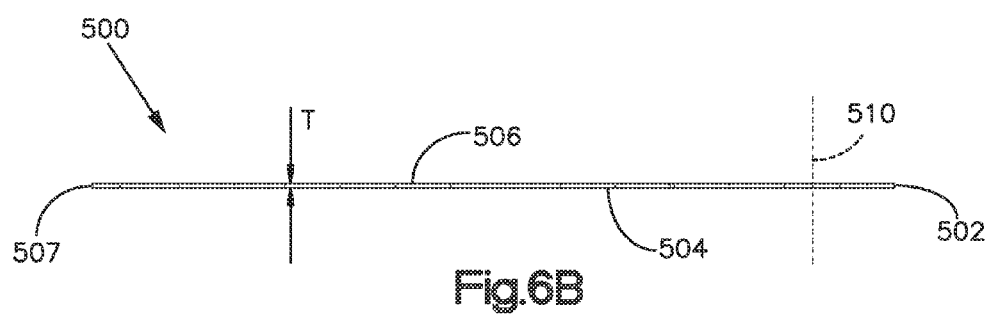
FIG. 6B is a side elevation view of the fixation device illustrated in FIG. 6A, the fixation device shown in the first flat configuration.
Figure 6C:
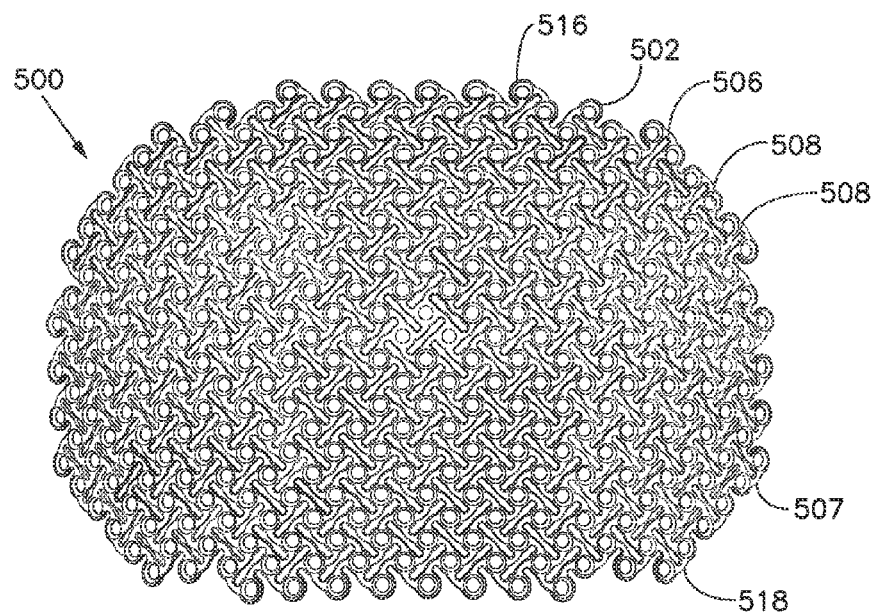
FIG. 6C is a top plan view of the fixation device illustrated in FIG. 6A, the fixation device shown in the second contoured configuration.
Figure 6D:
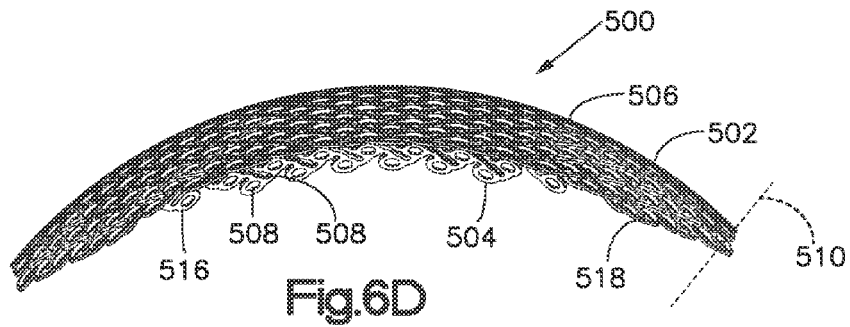
FIG. 6D is a side elevation view of the fixation device illustrated in FIG. 6C, the fixation device shown in the second contoured configuration.
Figure 6E:
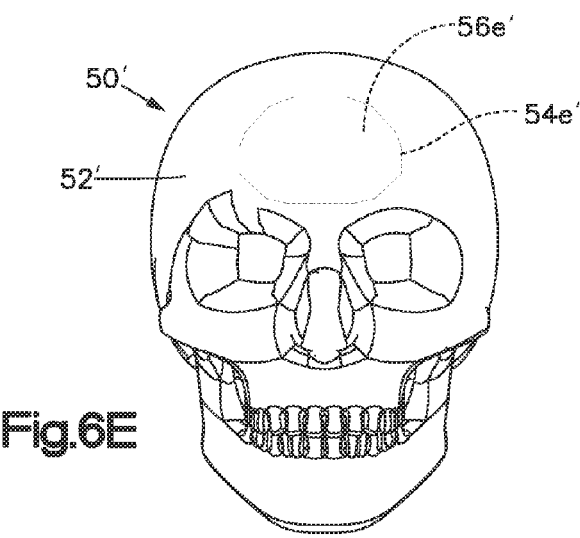
FIG. 6E is a front elevation view of a population averaged skull.
Figure 7A:
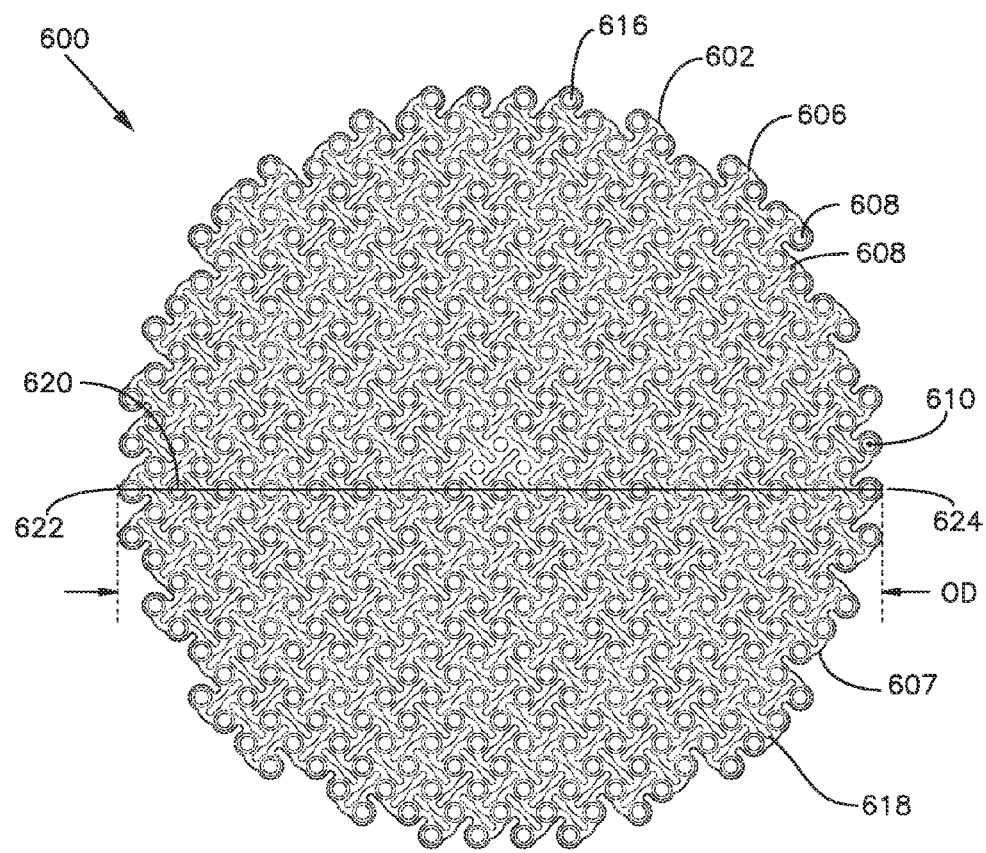
FIG. 7A is a top plan view of a fixation device according to another embodiment, the fixation device shown in the first flat configuration.
Figure 7B:
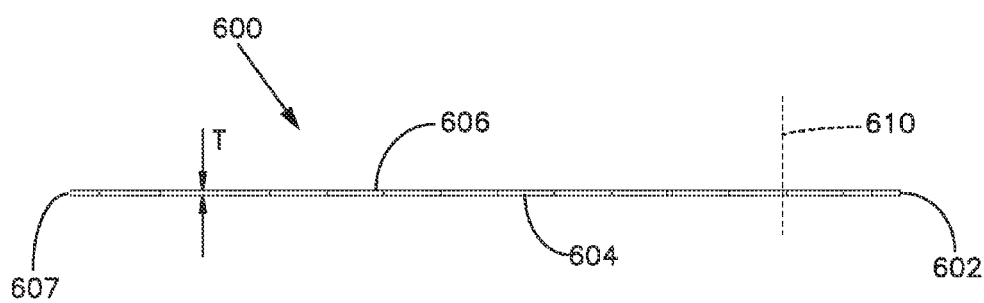
FIG. 7B is a side elevation view of the fixation device illustrated in FIG. 6A, the fixation device shown in the first flat configuration.
Figure 7C:
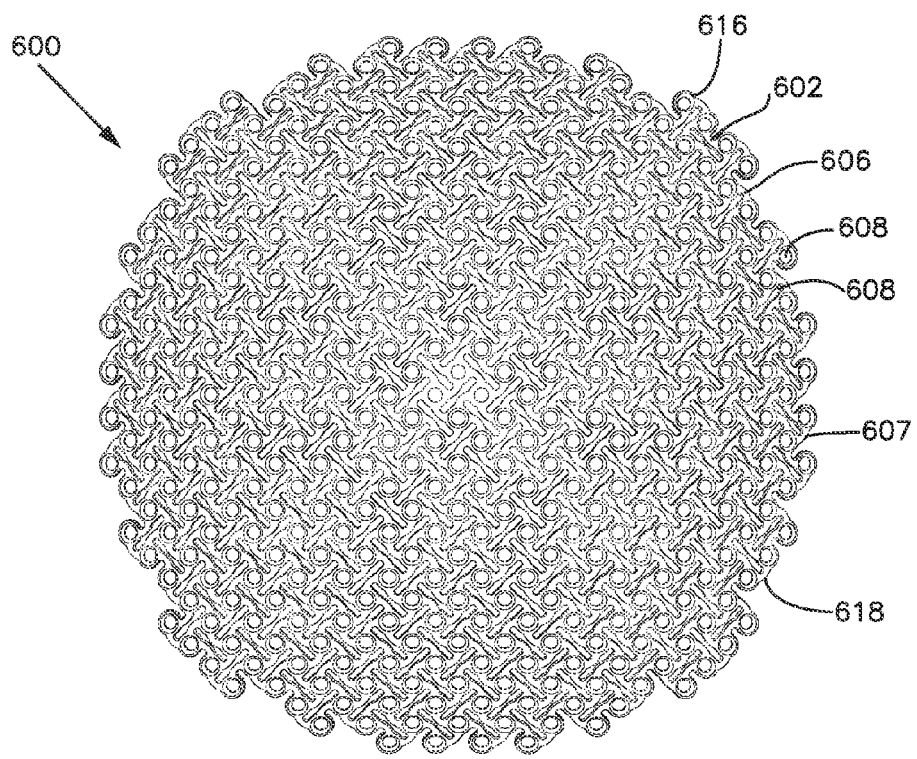
FIG. 7C is a top plan view of the fixation device illustrated in FIG. 6A, the fixation device shown in the second contoured configuration.
Figure 7D:
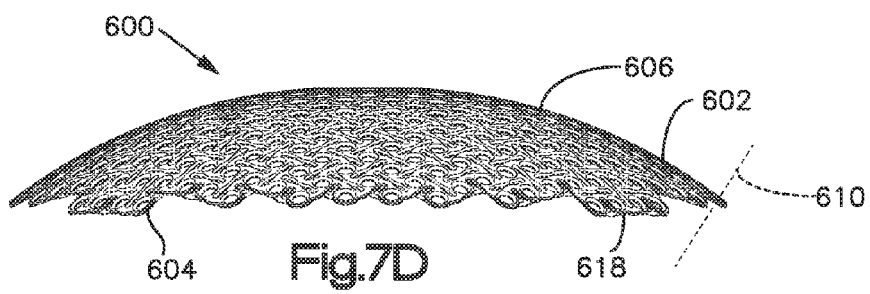
FIG. 7D is a side elevation view of the fixation device illustrated in FIG. 6C, the fixation device shown in the second contoured configuration.
Figure 7E:
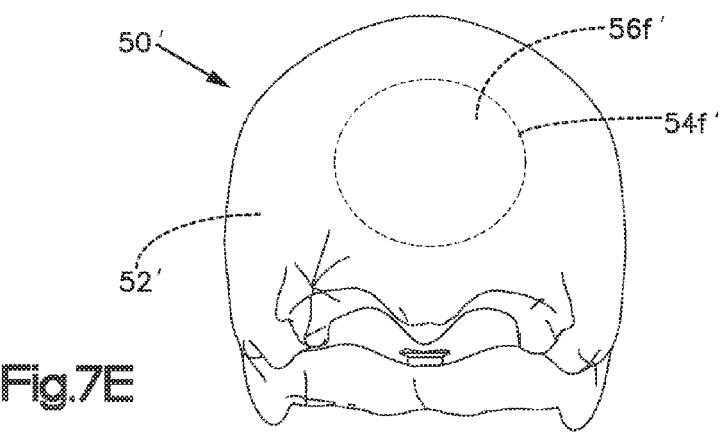
FIG. 7E is a rear elevation view of the population averaged skull illustrated in FIG. 4G.

Referring to FIGS. 5G to 5H, a fourth cranial mesh 400 is provided. The fourth cranial mesh 400 is similar to the cranial mesh 100 such that the entirety of the description of the cranial mesh 100 above, applies to the fourth cranial mesh 400. Structural elements in the fourth cranial mesh 400 that correspond to structural elements in the cranial mesh 100 are increased by three hundred, for example the fourth cranial mesh 400 can include a flexible mesh body 402, the flexible mesh body 402 having an inner surface 404, an outer surface 406 that is opposite the inner surface 404, a sidewall 407 that extends between the inner surface 404 and the outer surface 406. The fourth cranial mesh 400 can further include a plurality of apertures 408 that each defines a respective central axis 410. Each of the plurality of apertures 408 extends along the respective central axis 410 from the inner surface 404 to the outer surface 406.

According to one embodiment, the fourth cranial mesh 400 is the mirror image of the third cranial mesh 300. Thus, when the fourth cranial mesh 400 is in the second, contoured configuration, the inner surface 404 generally conforms to a fourth geometry 56d of the fourth region 54d of the skull 50, which as shown can be on the opposite side of the skull 50 from the third region 54c. As shown in the illustrated embodiment of FIGS. 5G to 5H, when the fourth cranial mesh 400 is in the second, contoured configuration, the inner surface 404 can generally conform to an averaged fourth geometry 56d' defined by the fourth region 54d' of the population averaged skull 50'.

Referring to FIGS. 6A to 6E, a fifth cranial mesh 500 is provided. The fifth cranial mesh 500 is similar to the cranial mesh 100 such that the entirety of the description of the cranial mesh 100 above, applies to the fifth cranial mesh 500. Structural elements in the fifth cranial mesh 500 that correspond to structural elements in the cranial mesh 100 have been labeled with reference numbers increased by four hundred. For example the fifth cranial mesh 500 can include a flexible mesh body 502, the flexible mesh body 502 having an inner surface 504, an outer surface 506 that is opposite the inner surface 504, a sidewall 507 that extends between the inner surface 504 and the outer surface 506. The fifth cranial mesh 500 can further include a plurality of apertures 508 that each defines a respective central axis 510. Each of the plurality of apertures 508 extends along the respective central axis 510 from the inner surface 504 to the outer surface 506.

According to one embodiment, the fifth cranial mesh 500 has a different size and shape compared to the cranial mesh 100. When the fifth cranial mesh 500 is in the second, contoured configuration, the inner surface 504 generally conforms to a fifth geometry 56e of the fifth region 54e of the skull 50. The fifth geometry 56e being different than each of the first geometry 56a, the second geometry 56b, the third geometry 56c, and the fourth geometry 56d. As shown in the illustrated embodiment of FIGS. 6C to 6E, when the fifth cranial mesh 500 is in the second, contoured configuration, the inner surface 504 can generally conform to an averaged fifth geometry 56e' defined by the fifth region 54e' of the population averaged skull 50'.

Referring to FIGS. 7A to 7E, a sixth cranial mesh 600 is provided. The sixth cranial mesh 600 is similar to the cranial mesh 100 such that the entirety of the description of the cranial mesh 100 above, applies to the sixth cranial mesh 600. Structural elements in the sixth cranial mesh 600 that correspond to structural elements in the cranial mesh 100 have been labeled with reference numbers increased by five hundred. For example the sixth cranial mesh 600 can include a flexible mesh body 602, the flexible mesh body 602 having an inner surface 604, an outer surface 606 that is opposite the inner surface 604, a sidewall 607 that extends between the inner surface 604 and the outer surface 606. The sixth cranial mesh 600 can further include a plurality of apertures 608 that each defines a respective central axis 610. Each of the plurality of apertures 608 extends along the respective central axis 610 from the inner surface 604 to the outer surface 606.

According to one embodiment, the sixth cranial mesh 600 has a different size and shape compared to the cranial mesh 100. When the sixth cranial mesh 600 is in the second, contoured configuration, the inner surface 604 generally conforms to a sixth geometry 56f of the sixth region 54f of the skull 50. The sixth geometry 56f is different than both the first, second, third, fourth, and fifth geometries 56a, 56b, 56c, 56d, and 56e. As shown in the illustrated embodiment of FIGS. 7C to 7E, when the sixth cranial mesh 600 is in the second, contoured configuration, the inner surface 604 can generally conform to an averaged sixth geometry 56f' defined by the sixth region 54f' of the population averaged skull 50'.

Figure 8A:
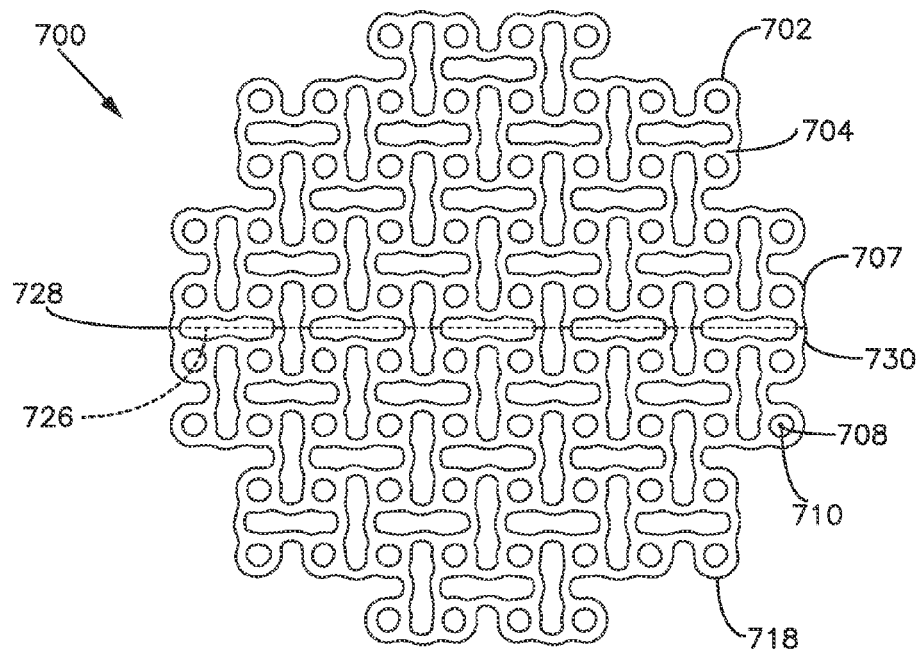
FIG. 8A is a bottom plan view of a fixation device according to another embodiment, the fixation device including a first surface and an outer perimeter, the fixation device defining a line that traces the first surface and intersects the outer perimeter at two points.
Figure 8B:
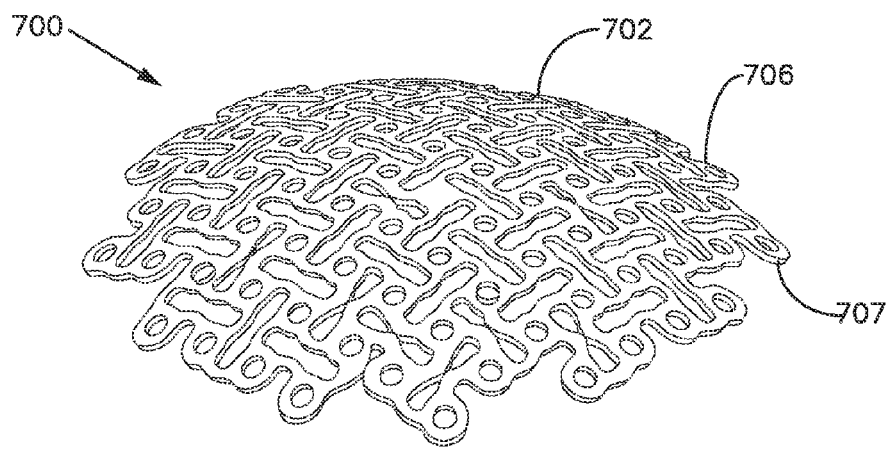
FIG. 8B is a perspective view of the fixation device illustrated in FIG. 8A.
Figure 8C:
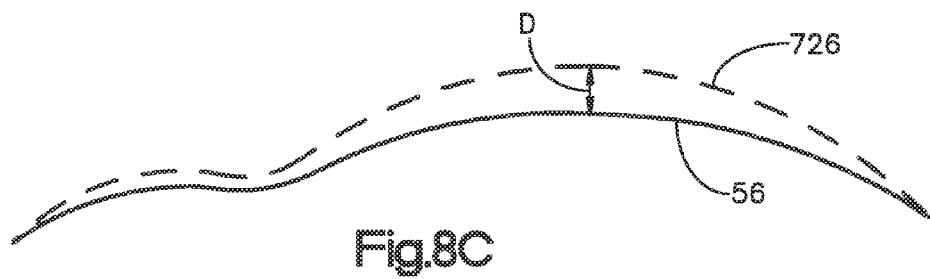
FIG. 8C is a side elevation view of the line illustrated in FIG. 8A and a line tracing a geometry.

Referring to FIGS. 8A to 8C, a seventh cranial mesh 700 is provided. The seventh cranial mesh 700 can include a flexible mesh body 702, the flexible mesh body 702 having an inner surface 704, an outer surface 706 that is opposite the inner surface 704, a sidewall 707 that extends between the inner surface 704 and the outer surface 706. In the illustrated embodiment, the inner surface 704 is the mirror image of the outer surface 706, and vice versa. The seventh cranial mesh 700 can further include a plurality of apertures 708 that each defines a respective central axis 710. Each of the plurality of apertures 708 extends along the respective central axis 710 from the inner surface 704 to the outer surface 706.

The mesh body 702 can further define an outer perimeter 718 that is defined by the sidewall 707. When the seventh cranial mesh 700 is in the second, contoured configuration, the mesh body 702 defines a line 726 that intersects the outer perimeter 718 at a first perimeter point 728 and a second perimeter point 730 spaced from the first perimeter point 728. As shown in the illustrated embodiment, the line 726 traces the inner surface 704 along a path between the first perimeter point 728 and the second perimeter point 730. The line 726 is interrupted (as shown by the dashed portions) by any of the plurality of apertures 708 along the traced path.

The mesh body 702 is configured as-manufactured to contact a geometry 56, for example a predetermined averaged geometry 56, at least at a first location, such that 1) no portion of the mesh body 702 crosses the predetermined averaged geometry 56 in a first direction from the outer surface 706 toward the inner surface 704, and 2) the mesh body 702 is devoid of a line 726 that defines a maximum distance D from the predetermined averaged geometry 56 greater than 20 mm, the line intersecting the outer perimeter 718 at both a first perimeter point 728 and a second perimeter point 730 spaced from the first perimeter point 728, the line 726 tracing the inner surface 704 along a path between the first perimeter point 728 and the second perimeter point 730. The description of the seventh cranial mesh 700 above is applicable to any of the other cranial mesh embodiments 100, 200, 300, 400, 500, 600 disclosed herein.

A kit of preformed cranial meshes is also provided. The kit can include one or more of any one or of any combination of the cranial mesh embodiments described herein. As merely one example, in one embodiment, the kit can include one or more of the cranial mesh 100 and one or more of the second cranial mesh 200. In another embodiment, the kit can include a plurality of the cranial mesh 100.

Referring to FIGS. 3A to 8C, a method of fabricating at least one cranial mesh, for example any of the cranial mesh embodiments described herein, to generally correspond to a predetermined averaged geometry is provided. Although described with reference to the cranial mesh 100, the following description of the method of fabricating at least one cranial mesh applies to each of the other embodiments of the cranial mesh 200, 300, 400, 500, 600, and 700 described herein.

In one embodiment, the method includes the steps of inserting a first sheet of flexible mesh, for example the cranial mesh 100 in the first flat configuration, between a first positive mold and a first negative mold that collectively define a first mold geometry, such that an inner surface 104 of the cranial mesh 100 faces the first positive mold and an outer surface 106 of the cranial mesh 100 faces the first negative mold. The method further comprises the step of bringing one or both of the first positive mold and the first negative mold toward the other of the first positive mold and the first negative mold so as to bend a portion of the cranial mesh 100 to a first bent shape that corresponds to the first positive mold and the first negative mold. In one embodiment, the method comprises securing the outer perimeter 118 of the cranial mesh 100 during the bringing step, such that as the portion of the cranial mesh 100 is bent, the size and shape of the outer perimeter 118 remains unchanged. After the completion of the bringing step and the securing step, the inner surface 104 defines a first mesh geometry that corresponds to a predetermined averaged geometry such that when the cranial mesh 100 contacts the predetermined averaged geometry at least at one location, 1) no portion of the mesh body 102 crosses the predetermined averaged geometry in a first direction from the outer surface 106 toward the inner surface 104, and 2) no location on the inner surface 104 of the mesh body 102 is spaced from the predetermined averaged geometry a distance greater than 20 mm.

According to one embodiment the method can further comprise the step of changing the size and shape of one or more of the apertures 108 within the portion of the cranial mesh 100 that is being bent. In one embodiment, the apertures 108 that change shape are non-circular holes that extend through the upper surface 106 and the lower surface 104. In one embodiment, the non-circular holes are non-fastener receiving holes.

In one embodiment of the method described above, the predetermined averaged geometry is defined by a population averaged geometry of a population averaged human skull 50, such that the method can further include the step of positioning the cranial mesh 100 adjacent the predetermined averaged geometry such that: 1) at least a portion of the inner surface 104 abuts the population averaged skull 50, and 2) every point on the inner surface 104 of the cranial mesh 100 is separated from the population averaged skull 50 by a distance of 20 mm or less, for example 10 mm or less, or 3 mm or less. According to one embodiment of the method the positioning step is performed prior to inserting any fasteners through the cranial mesh 100 and into the predetermined averaged geometry to affix the cranial mesh 100 to the predetermined averaged geometry. In one embodiment, all of the steps of the method are performed without the application of an external heat source to the cranial mesh 100.

In another embodiment, the method further includes the step of inserting a second sheet of flexible mesh, for example the cranial mesh 200 in the first flat configuration, between a second positive mold and a second negative mold that collectively define a second mold geometry, such that an inner surface 204 of the cranial mesh 200 faces the second positive mold and an outer surface 206 of the cranial mesh 200 faces the second negative mold. The method further comprises the step of bringing one or both of the second positive mold and the second negative mold toward the other of the second positive mold and the second negative mold so as to bend a portion of the cranial mesh 200 to a second bent shape that corresponds to the second positive mold and the second negative mold. In one embodiment, the method comprises securing the outer perimeter 218 of the cranial mesh 200 during the bringing step, such that as the portion of the cranial mesh 200 is bent, the size and shape of the outer perimeter 218 remains substantially unchanged. After the completion of the bringing step and the securing step, the inner surface 204 defines a second mesh geometry that corresponds to a second predetermined averaged geometry such that when the cranial mesh 200 contacts the second predetermined averaged geometry at least at one location, 1) no portion of the mesh body 202 crosses the predetermined averaged geometry in a second direction from the outer surface 206 toward the inner surface 204, and 2) no location on the inner surface 204 of the mesh body 202 is spaced from the predetermined averaged geometry a distance greater than 20 mm, for example 10 mm or less, or 3 mm or less.

It will be appreciated by those skilled in the art that changes could be made to the embodiments described above without departing from the broad inventive concept thereof. It is understood, therefore, that this disclosure is not limited to the particular embodiments disclosed, but it is intended to cover modifications within the spirit and scope of the present disclosure as defined by the claims.

What is claimed:

1. A cranial mesh configured to generally conform to a predetermined averaged geometry, the cranial mesh comprising:
   a preformed flexible mesh body having an inner surface, an outer surface opposite the inner surface, and a plurality of apertures that extend through the preformed flexible mesh body from the outer surface to the inner surface, each of the plurality of apertures extending along a respective central axis from the outer surface to the inner surface,
   wherein the preformed flexible mesh body is configured as-manufactured to contact the predetermined averaged geometry at least at three spaced apart locations, such that 1) no portion of the preformed flexible mesh body crosses the predetermined averaged geometry in a first direction from the outer surface toward the inner surface, and 2) no location on the inner surface of the preformed flexible mesh body is spaced from the predetermined averaged geometry a distance greater than 20 mm along the first direction.

2. The cranial mesh of claim 1, wherein no location on the inner surface of the preformed flexible mesh body is spaced from the predetermined averaged geometry a distance greater than 10 mm along the first direction.

3. The cranial mesh of claim 2, wherein no location on the inner surface of the preformed flexible mesh body is spaced from the predetermined averaged geometry a distance greater than 3 mm along the first direction.

4. The cranial mesh of claim 1, wherein the distance is measured from a given location on the inner surface to the predetermined averaged geometry along a direction parallel to the respective central axis of a respective one of the plurality of apertures closest to the given location.

5. The cranial mesh of claim 1, wherein the predetermined averaged geometry is a population averaged geometry of a plurality of human skull geometries.

6. The cranial mesh of claim 1, wherein the preformed flexible mesh body has a thickness measured from a first location on the inner surface to the outer surface along a direction parallel to the respective central axis of a respective one of the plurality of apertures closest to the first location of the inner surface, the thickness within the range of about 0.8 mm to about 0.4 mm.

7. The cranial mesh of claim 1, wherein the plurality of apertures includes a plurality of holes that are each configured to receive a fastener that secures the cranial mesh to the predetermined averaged geometry.

8. A cranial mesh configured to generally conform to a predetermined averaged geometry, the cranial mesh comprising:
   a preformed flexible mesh body having an inner surface, an outer surface opposite the inner surface, and a plurality of apertures that extend through the preformed flexible mesh body from the outer surface to the inner surface, each of the plurality of apertures extending along a respective central axis from the outer surface to the inner surface, the preformed flexible mesh body including a sidewall that extends between the inner surface and the outer surface, the sidewall defining an outer perimeter of the preformed flexible mesh body, the outer perimeter having a maximum outer dimension measured along a straight line from a first point on the outer perimeter to a second point on the outer perimeter, such that the preformed flexible mesh body does not define an outer dimension measured along a straight line that extends between and terminates at any pair of points on the outer perimeter that is greater than the maximum outer dimension;
   wherein the preformed flexible mesh body is configured as-manufactured such that when the inner surface contacts the predetermined averaged geometry at least at three spaced apart locations, 1) no portion of the preformed flexible mesh body crosses the predetermined averaged geometry in a direction from the outer surface toward the inner surface, and 2) no location on the inner surface is spaced from the predetermined averaged geometry a distance greater than 10 percent of the maximum outer dimension as measured along a straight line that defines a shortest distance to the predetermined averaged geometry.

9. The cranial mesh of claim 8, wherein no location on the inner surface is spaced from the predetermined averaged geometry a distance greater than 5 percent of the maximum outer dimension as measured along a straight line that defines a shortest distance to the predetermined averaged geometry.

10. The cranial mesh of claim 9, wherein no location on the inner surface is spaced from the predetermined averaged geometry a distance greater than 3 percent of the maximum outer dimension as measured along a straight line that defines a shortest distance to the predetermined averaged geometry.

11. The cranial mesh of claim 8, wherein the distance is measured from a given location on the inner surface to the outer surface along a direction parallel to the respective central axis of a respective one of the plurality of apertures closest to the given location.

12. The cranial mesh of claim 8, wherein the predetermined averaged geometry is a population averaged geometry of a plurality of human skull geometries.

13. The cranial mesh of claim 8, wherein the preformed flexible mesh body has a thickness measured from a first location on the inner surface to the outer surface along a direction parallel to the respective central axis of a respective one of the plurality of apertures closest to the first location of the inner surface, the thickness within the range of about 0.8 mm to about 0.4 mm.

14. The cranial mesh of claim 8, wherein the plurality of apertures includes a plurality of holes that are each configured to receive a fastener that secures the cranial mesh to the predetermined averaged geometry.

15. A package comprising:
   a package body defining an enclosed interior; and
   a cranial mesh disposed in the enclosed interior, the cranial mesh configured to generally conform to a predetermined averaged geometry, the cranial mesh comprising:
   a preformed flexible mesh body having an inner surface, an outer surface opposite the inner surface, and a plurality of apertures that extend through the preformed flexible mesh body from the outer surface to the inner surface, each of the plurality of apertures extending along a respective central axis from the outer surface to the inner surface,
   wherein the preformed flexible mesh body is configured as-manufactured to contact the predetermined averaged geometry at least at three spaced apart locations, such that 1) no portion of the preformed flexible mesh body crosses the predetermined averaged geometry in a first direction from the outer surface toward the inner surface, and 2) no location on the inner surface of the preformed flexible mesh body is spaced from the predetermined averaged geometry a distance greater than 20 mm along the first direction.

16. The package of claim 15, wherein the interior is a sterile interior.

17. The package of claim 15, wherein the distance is measured from a given location on the inner surface to the predetermined averaged geometry along a direction parallel to the respective central axis of a respective one of the plurality of apertures closest to the given location.

18. The package of claim 15, wherein the predetermined averaged geometry is a population averaged geometry of a plurality of human skull geometries.

19. The package of claim 15, wherein the preformed flexible mesh body has a thickness measured from a first location on the inner surface to the outer surface along a direction parallel to the respective central axis of a respective one of the plurality of apertures closest to the first location of the inner surface, the thickness within the range of about 0.8 mm to about 0.4 mm.

20. The package of claim 15, wherein the plurality of apertures includes a plurality of holes that are each configured to receive a fastener that secures the cranial mesh to the predetermined averaged geometry.

21. A kit of preformed cranial meshes, each of the preformed cranial meshes configured to generally conform to different regions of a predetermined averaged geometry, the kit comprising:
   a first preformed flexible cranial mesh having a first inner surface, a first outer surface that is opposite the first inner surface, and a first plurality of apertures that extend from the first outer surface to the first inner surface, the first preformed flexible cranial mesh configured as-manufactured such that when the first inner surface contacts a first region of the predetermined averaged geometry, no location on the first inner surface is spaced from the predetermined averaged geometry by more than 20 mm; and a second preformed flexible cranial mesh having a second inner surface, a second outer surface that is opposite the second inner surface, and a second plurality of apertures that extend from the second outer surface to the second inner surface, the second preformed flexible cranial mesh configured as-manufactured such that when the second inner surface contacts a second region of the predetermined averaged geometry that is spaced from the first region, no location on the second inner surface is spaced from the predetermined averaged geometry by more than 20 mm.

22. The kit of claim 21, wherein the first preformed flexible cranial mesh is configured as-manufactured such that when the first inner surface contacts the first region of the predetermined averaged geometry, no location on the first inner surface is spaced from the predetermined averaged geometry by more than 3 mm.

23. The kit of claim 21, wherein the second preformed flexible cranial mesh is configured as-manufactured such that when the second inner surface contacts the second region of the predetermined averaged geometry, no location on the second inner surface is spaced from the predetermined averaged geometry by more than 3 mm.

24. The kit of claim 21, further comprising a third preformed flexible cranial mesh having a third inner surface, a third outer surface that is opposite the third inner surface, and a third plurality of apertures that extend from the third outer surface to the third inner surface, the third preformed flexible cranial mesh configured as-manufactured such that when the third inner surface contacts a third region of the predetermined averaged geometry that is spaced from the first and second regions, no location on the third inner surface is spaced from the predetermined averaged geometry by more than 20 mm.

25. The kit of claim 24, wherein the third preformed flexible cranial mesh is configured as-manufactured such that when the third inner surface contacts the third region of the predetermined averaged geometry, no location on the third inner surface is spaced from the predetermined averaged geometry by more than 3 mm.

26. The kit of claim 24, further comprising a fourth preformed flexible cranial mesh having a fourth inner surface, a fourth outer surface that is opposite the fourth inner surface, and a fourth plurality of apertures that extend from the fourth outer surface to the fourth inner surface, the fourth preformed flexible cranial mesh is configured as-manufactured such that when the fourth inner surface contacts a fourth region of the predetermined averaged geometry that is spaced from the first, second, and third regions, no location on the fourth inner surface is spaced from the predetermined averaged geometry by more than 20 mm.

27. The kit of claim 26, wherein the fourth preformed flexible cranial mesh is configured as-manufactured such that when the fourth inner surface contacts the fourth region of the predetermined averaged geometry, no location on the fourth inner surface is spaced from the predetermined averaged geometry by more than 3 mm.

28. The kit of claim 21, wherein the predetermined averaged geometry is a population averaged geometry of a plurality of human skull geometries.

29. The kit of claim 28, wherein the first region is defined by the geometry of a population averaged geometry of a plurality of parietal bones, the second region is defined by the geometry of a population averaged geometry of a plurality of temporal bones, the third region is defined by the geometry of a population averaged geometry of a plurality of frontal bones, and the fourth region is defined by the geometry of a population averaged geometry of a plurality of occipital bones.

30. The kit of claim 21, wherein the first preformed flexible cranial mesh is configured as-manufactured such that when the first inner surface contacts the first region of the predetermined averaged geometry, a first point on the first inner surface defines a minimum distance from the predetermined averaged geometry, and the minimum distance is equal to 0 mm.

* * * * *